(12) United States Patent
Ueda et al.

(10) Patent No.: US 7,910,362 B2
(45) Date of Patent: Mar. 22, 2011

(54) REPORTER VECTOR FOR USE IN EVALUATION OF CYP1A2 INDUCTION

(75) Inventors: Rika Ueda, Tsukuba (JP); Kazutomi Kusano, Tsukuba (JP); Yasushi Yamazoe, Sendai (JP); Kiyoshi Nagata, Sendai (JP)

(73) Assignees: Eisai R&D Management Co., Ltd., Tokyo (JP); Tohoku University, Sendai-shi (JP)

( * ) Notice: Subject to any disclaimer, the term of this patent is extended or adjusted under 35 U.S.C. 154(b) by 267 days.

(21) Appl. No.: 11/995,398

(22) PCT Filed: Jul. 12, 2006

(86) PCT No.: PCT/JP2006/313904
§ 371 (c)(1),
(2), (4) Date: Feb. 13, 2008

(87) PCT Pub. No.: WO2007/007810
PCT Pub. Date: Jan. 18, 2007

(65) Prior Publication Data
US 2009/0317800 A1    Dec. 24, 2009

(30) Foreign Application Priority Data

Jul. 12, 2005  (JP) ................................. 2005-202813
Jan. 5, 2006   (JP) ................................. 2006-000454

(51) Int. Cl.
*C12N 15/63* (2006.01)
*C07H 21/04* (2006.01)

(52) U.S. Cl. ..................... 435/320.1; 435/325; 435/70.1; 536/24.1

(58) Field of Classification Search .......................... None
See application file for complete search history.

(56) References Cited

OTHER PUBLICATIONS

Injae Chung, et al., "Regulation of the Constitutive Expression of the Human CYP1A2 Gene: Cis Elements and Their Interactions with Proteins", Molecular Pharmacology, vol. 47, No. 4, XP-009012315, Jan. 1, 1995, pp. 677-685.

Linda C. Quattrochi, et al., "Induction of the Human CYP1A2 Enhancer by Phorbol Ester", Archives of Biochemistry and Biophysics, vol. 350. No. 1, XP-002508271, Feb. 1, 1998, pp. 41-48.

Injae Chung, et al., "No Role of Protected Region B of Human Cytochrome P4501A2 Gene (CYP1A2) As an AP-1 Response Element.", Archives of Pharmacal Research, vol. 25, No. 3, XP-002508272, Jun. 2002, pp. 375-380.

Virginia H. Black, et al., "Molecular Cloning of the Guinea Pig CYP1A2 Gene 5' -Flanking Region: Identification of Functional Aromatic Hydrocarbon Response Element and Characterization of CYP1A2 Expression in GPC16 Cells", Drug Metabolism and Disposition, vol. 32, No. 6, XP-002508273, Jun. 1, 2004, pp. 595-602.

Corchero, et al., Organization of the CYP1A cluster on human chromosome 15: implications for gene regulation, Pharmacogenetics, vol. 11, No. 1, pp. 1-6. 2001.

Quattrochi, et al., "The Human CYP1A2 Gene and Induction by 3-Methylcholanthrene", The Journal of Biological Chemistry, vol. 269, No. 9, pp. 6949-6954, 1994.

Postlind, et al., Response of Human CYP1-Luciferase Plasmids to 2,3,7,8-Tetrachlorodibenzo-p-dioxin and Polycyclic Aromatic Hydrocarbons[1] Toxicology and Applied Pharmacology, vol. 118, No. 2, pp. 255-262, 1993.

Ueda, et al., "A Common Regulatory Region Functions Bidirectionally in Transcriptional Activation of the Human CYP1A1 and CYP1A2 Genes", Molecular Pharmacology, vol. 69, No. 6, pp. 1924-1930, 2006.

James P. Whitlock, Jr., "Induction of Cytochrome P4501A1", Annual Review of Pharmacology and Toxicology, 1999, vol. 39, pp. 103-125.

P. M. Garrison, et al., "Species-Specific Recombinant Cell Lines as Bioassay Systems for the Detection of 2,3,7,8-Tetrachlorodibenzo-p-dioxin-like Chemicals", Fundamental and Applied Toxicology, vol. 30, No. 2, Apr. 1996, pp. 194-203.

Erin E. Bessette, et al., "Mechanisms of Arsenite-Mediated Decreases in Benzo[K]Fluoranthene-induced Human Cytochrome P4501A1 Levels in HEPG2 Cells", Drug Metabolism and Disposition, vol. 33, No. 3, 2005, pp. 312-320.

David L. Eaton, et al., "Role of Cytochrome P4501A2 in Chemical Carcinogenesis: Implications for Human Variability in Expression and Enzyme Activity", Pharmacogenetics (1995) 5, pp. 259-274.

Rika Ueda, et al., "A Common Regulatory Region Functions Bidirectionally in Transcriptional Activation of the Human CYP1A1 and CYP1A2 Genes", Molecular Pharmacology, vol. 69, No. 6, 2006, pp. 1924-1930.

*Primary Examiner* — Celine X Qian
(74) *Attorney, Agent, or Firm* — Oblon, Spivak, McClelland, Maier & Neustadt, L.L.P.

(57) ABSTRACT

A reporter vector which can evaluate the ability of a drug to induce CYP1A2 or both of CYP1A1 and CYP1A2 and a method for evaluation of the ability of a drug to induce CYP1A2 or both of CYP1A1 and CYP1A2 by using the reporter vector. A reporter system which can evaluate the ability of a drug capable of inducing CYP1A2 or both of CYP1A1 and CYP1A2 is completed by constructing a reporter vector having a reporter gene linked to the 3' end of a region between CYP1A1 and CYP1A2 or a reporter vector having different reporter genes linked to the both ends of the region, respectively, so as to sandwich the region, and a reporter vector having a deletion mutation in the region, and confirming that the expression of a reporter molecule is increased by the drug capable of inducing CYP1A2 or both of CYP1A1 and CYP1A2 in the reporter system using the reporter vector.

8 Claims, 6 Drawing Sheets

REPORTER VECTOR FOR USE IN EVALUATION OF CYP1A2 INDUCTION

CROSS-REFERENCE TO RELATED APPLICATIONS

The present application is a 35 U.S.C. §371 National Stage patent application of International patent application PCT/JP2006/313904, filed on Jul. 12, 2006, which claims priority to Japanese patent applications JP 2006-000454, filed on Jan. 5, 2006, and JP 2005-202813, filed on Jul. 12, 2005.

TECHNICAL FIELD

The present invention relates to an expression vector which enables the evaluation of human CYP1A2 induction by a drug, and a method for evaluating the human CYP1A2 induction using this expression vector.

The present invention further relates to an expression vector which enables simultaneous evaluation of the induction of both human CYP1A1 and CYP1A2, and a method for evaluating the induction of human CYP1A1 and CYP1A2 using the expression vector.

BACKGROUND ART

Induction of drug-metabolizing enzymes is one of the mechanisms for drug-drug interaction. In general, the induction of the enzyme is caused by the increase of transcription of a drug-metabolizing enzyme gene, and in order to evaluate induction of the enzyme, screening is performed by using a recombinant reporter vector prepared by incorporating a part of a regulatory region of a drug-metabolizing enzyme gene into a 5' upstream region of a reporter gene.

Cytochrome P450 (CYP), a major drug-metabolizing enzyme, consists of a gene superfamily, and there are many isozymes with different substrate specificities (Non-patent document 1). Among them, the CYP1A family is involved not only in metabolism of drug but also in metabolic activation of carcinogens such as polycyclic hydrocarbons and aromatic amines.

It is known that human CYP1A1 and CYP1A2 genes adjacently exist on the chromosome 15 in reverse directions (Non-patent document 2). For CYP1A1, a region which is responsible for the induction thereof by a drug is well-characterized (Non-patent document 3), and reporter systems that enable the evaluation of the induction by a drug have also been constructed (Non-patent documents 4 to 6). However, for CYP1A2, although it is known that the proximal region of the CYP1A2 gene is not enough for the induction thereof (Non-patent document 7), and it is not specified which regions are involved in the induction of CYP1A2.

Non-patent document 1: Pharmacogenetics, 6:1-42 (1996)
Non-patent document 2: Pharmacogenetics, 11:1-6 (2001)
Non-patent document 3: Ann. Rev. Pharmacol. Toxicol., 39:103-125 (1999)
Non-patent document 4: Toxicol. Appl. Pharmacol., 118:255-262 (1993)
Non-patent document 5: Fundam. Appl. Toxicol., 30:194-203 (1996)
Non-patent document 6: Drug Metab. Dispos., 33:312-320 (2005)
Non-patent document 7: Pharmacogenetics, 5:259-274 (1995)

DISCLOSURE OF THE INVENTION

An object of the present invention is to identify a transcriptional regulatory region which is responsible for the induction of CYP1A2 by a drug, to construct a reporter vector which enables the evaluation of CYP1A2 induction by a drug, using that region, and to provide a method for evaluating CYP1A2 induction by using this reporter vector.

Another object of the present invention is to construct an expression vector which enables simultaneous evaluation of induction of CYP1A1 as well as CYP1A2, and to provide a method for simultaneously evaluating the human CYP1A1 and CYP1A2 induction by using this expression vector.

The inventors of the present invention first constructed an expression vector comprising a 23 kb-intergenic region between the CYP1A1 and CYP1A2 gene, in which different reporter genes are added at both the ends of the region (henceforth also referred to the expression vector of the present invention), so that the transcriptional regulation of the CYP1A1 and CYP1A2 genes should be reflected in the reporter system in a state as close as possible to that in living bodies. Then, it was confirmed that drugs known to have ability to induce CYP1A1 and CYP1A2 increased expression of the reporter genes by an experiment using a reporter system comprising the expression vector.

Then, the inventors of the present invention found that induction of CYP1A2 by a drug could not be observed only with the proximal 5'-upstream transcriptional regulatory region of CYP1A2, and deletion of a region neighboring CYP1A1 between both the genes diminished not only the induction of CYP1A1 but also the induction of CYP1A2. They further found that the region neighboring CYP1A1 was essential for the induction of CYP1A2, and with the construction of the expression vector of the present invention including the region neighboring CYP1A1, in which a large number of xenobiotic responsive elements (XREs) are distributed, a reporter system reflecting the CYP1A1 and CYP1A2 induction could be constructed, and thus accomplished the present invention.

The reporter system enabled evaluation of induction of both CYP1A1 and CYP1A2 in a cell to which the expression vector of the present invention is introduced, and since it enabled simultaneous evaluation of induction of both CYP1A1 and CYP1A2, it also had an advantage that the improvement in operation efficiency could be expected.

The present invention thus relates to the followings.

An expression vector comprising a reporter gene operably linked to the 3' end of any one of DNAs of the following (a) to (e):

(a) a DNA comprising the nucleotide sequence of the nucleotide numbers 1925 to 2866 in SEQ ID NO: 1, (b) a DNA comprising a nucleotide sequence of the nucleotide numbers 1 to 2866 in SEQ ID NO: 1 including deletion, substitution or addition of one or more nucleotides, which increases expression of the reporter gene operably linked to the 3' end in the presence of a drug which induces CYP1A2, (c) a DNA comprising a nucleotide sequence having a homology of 90% or more to the nucleotide sequence of the nucleotide numbers 1 to 2866 in SEQ ID NO: 1, which increases expression of the reporter gene operably linked to the 3' end in the presence of a drug which induces CYP1A2, (d) a DNA comprising a DNA hybridizable with a DNA comprising a nucleotide sequence complementary to the nucleotide sequence of the nucleotide numbers 1 to 2866 in SEQ ID NO: 1, which increases expression of the reporter gene operably linked to the 3' end in the presence of a drug which induces CYP1A2, and (e) a DNA comprising the nucleotide sequence of the nucleotide numbers 5659 to 9180 in SEQ ID NO: 1.

The expression vector according to [1], wherein the DNA is a DNA comprising any one of the nucleotide sequences of the following (1) to (9):
(1) the nucleotide sequence of the nucleotide numbers 1242 to 2866 in SEQ ID NO: 1,
(2) the nucleotide sequence of the nucleotide numbers 1 to 2866 in SEQ ID NO: 1,
(3) the nucleotide sequence of the nucleotide numbers 1 to 5658 in SEQ ID NO: 1,
(4) the nucleotide sequence of the nucleotide numbers 1 to 9690 in SEQ ID NO: 1,
(5) the nucleotide sequence of the nucleotide numbers 1 to 19946 in SEQ ID NO: 1,
(6) the nucleotide sequence of the nucleotide numbers 1925 to 6117 in SEQ ID NO: 1,
(7) the nucleotide sequence of the nucleotide numbers 1925 to 24448 in SEQ ID NO: 1,
(8) a nucleotide sequence comprising a nucleotide sequence of the nucleotide numbers 1 to 5658 in SEQ ID NO: 1 including deletion of any of the nucleotide sequence of the nucleotide numbers 1535 to 1541, the nucleotide sequence of the nucleotide numbers 1930 to 1936, the nucleotide sequence of the nucleotide numbers 2018 to 2024, the nucleotide sequence of the nucleotide numbers 2093 to 2099, and the nucleotide sequence of the nucleotide numbers 2411 to 2417, and
(9) the nucleotide sequence of the nucleotide numbers 5659 to 24448 in SEQ ID NO: 1.

The expression vector according to [2], wherein the DNA is a DNA further comprising any one of the nucleotide sequences of the following (10) to (15):
(10) the nucleotide sequence of the nucleotide numbers 23697 to 24448 in SEQ ID NO: 1,
(11) the nucleotide sequence of the nucleotide numbers 23030 to 24448 in SEQ ID NO: 1,
(12) the nucleotide sequence of the nucleotide numbers 22167 to 24448 in SEQ ID NO: 1,
(13) the nucleotide sequence of the nucleotide numbers 19134 to 24448 in SEQ ID NO: 1,
(14) the nucleotide sequence of the nucleotide numbers 1925 to 24448 in SEQ ID NO: 1, and
(15) a nucleotide sequence of a DNA hybridizable with a DNA comprising a nucleotide sequence complementary to the nucleotide sequence of the nucleotide numbers 19134 to 24448 in SEQ ID NO: 1 under a stringent condition.

The expression vector according to [1], wherein the DNA is a DNA consisting of the nucleotide sequence of the nucleotide numbers 1242 to 2866 and the nucleotide sequence of the nucleotide numbers 23697 to 24448 in SEQ ID NO: 1.

The expression vector according to [1], wherein the DNA is a DNA comprising the nucleotide sequence of the nucleotide numbers 1 to 2866 and the nucleotide sequence of the nucleotide numbers 23030 to 24448 in SEQ ID NO: 1 ligated to each other.

The expression vector according to [1], wherein the DNA is a DNA comprising the nucleotide sequence of the nucleotide numbers 1 to 2866 and the nucleotide sequence of the nucleotide numbers 22167 to 24448 in SEQ ID NO: 1 ligated to each other.

The expression vector according to [1], wherein the DNA is a DNA comprising the nucleotide sequence of the nucleotide numbers 1 to 5658 and the nucleotide sequence of the nucleotide numbers 23030 to 24448 in SEQ ID NO: 1 ligated to each other.

The expression vector according to [1], wherein the DNA is a DNA comprising the nucleotide sequence of the nucleotide numbers 1 to 5658 and the nucleotide sequence of the nucleotide numbers 19134 to 24448 in SEQ ID NO: 1 ligated to each other.

The expression vector according to [1], wherein the DNA is a DNA comprising the nucleotide sequence of the nucleotide numbers 1 to 9690 and the nucleotide sequence of the nucleotide numbers 19134 to 24448 in SEQ ID NO: 1 ligated to each other.

The expression vector according to [1], wherein the DNA is a DNA comprising the nucleotide sequence of the nucleotide numbers 1 to 19946 and the nucleotide sequence of the nucleotide numbers 23030 to 24448 in SEQ ID NO: 1 ligated to each other.

The expression vector according to [1], wherein the DNA is a DNA consisting of the nucleotide sequence of the nucleotide numbers 1 to 24448 in SEQ ID NO: 1.

The expression vector according to [1], wherein the DNA is a DNA comprising the nucleotide sequence of the nucleotide numbers 1925 to 6117 and the nucleotide sequence of the nucleotide numbers 19134 to 24448 in SEQ ID NO: 1 ligated to each other.

The expression vector according to [1], wherein the DNA is a DNA consisting of the nucleotide sequence of the nucleotide numbers 1925 to 24448 in SEQ ID NO: 1.

The expression vector according to [1], wherein the DNA is a DNA comprising a nucleotide sequence of the nucleotide numbers 1 to 5658 in SEQ ID NO: 1 including deletion of any of the nucleotide sequence of the nucleotide numbers 1535 to 1541, the nucleotide sequence of the nucleotide numbers 1930 to 1936, the nucleotide sequence of the nucleotide numbers 2018 to 2024, the nucleotide sequence of the nucleotide numbers 2093 to 2099 and the nucleotide sequence of the nucleotide numbers 2411 to 2417, and the nucleotide sequence of the nucleotide numbers 23030 to 24448 ligated to each other.

The expression vector according to [1], wherein the DNA is a DNA comprising the nucleotide sequence of the nucleotide numbers 1 to 1241 and the nucleotide sequence of the nucleotide numbers 5659 to 24448 in SEQ ID NO: 1 ligated to each other.

A host cell to which the expression vector according to any one of [1] to [15] is introduced.

A method for measuring ability of a test drug to induce CYP1A2, which comprises (1) the step of culturing the host cell according to [16] in the presence of the test drug, (2) the step of measuring expression amount of the reporter gene, and (3) the step of determining that the test drug has an ability to induce CYP1A2, when the expression amount is affected as compared with the expression amount observed in the absence of the test drug.

The expression vector according to any one of [1] to [15], wherein the DNA is a DNA which increases expression of the reporter gene operably linked to the 5' end in the presence of a drug which induces CYP1A1, and is operably linked at the 5' end with a reporter gene different from that linked to the 3' end.

A host cell to which the expression vector according to [18] is introduced.

A method for measuring abilities of a test drug to induce CYP1A1 and CYP1A2, which comprises (1) the step of culturing the host cell according to [19] in the presence of the test drug, (2) the step of measuring expression amounts of the reporter genes, and (3) the step of determining that the test drug has abilities to induce CYP1A1 and CYP1A2, when the expression amounts are affected as compared with the expression amounts observed in the absence of the test drug.

According to the present invention, evaluation of ability of a drug to induce CYP1A2 is made easy, and when the expression vector is linked to a reporter gene also at the 5' end, simultaneous evaluation of CYP1A1 and CYP1A2 induction is enabled. Improvement in operational efficiency can be thus expected.

BEST MODE FOR CARRYING OUT THE INVENTION

Figure 1:
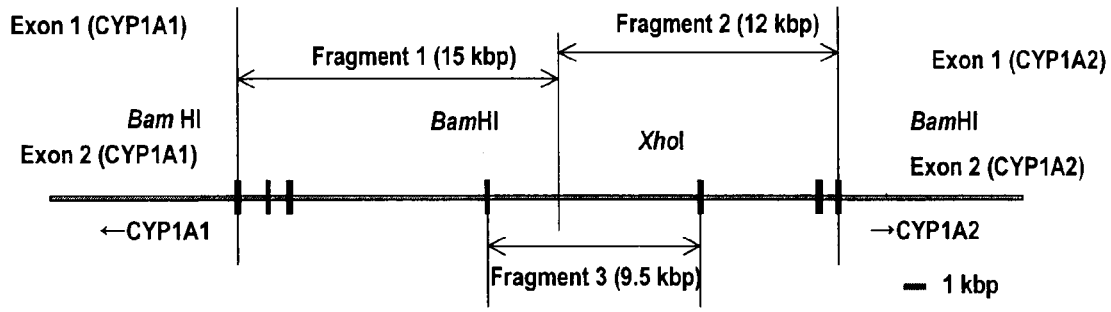
FIG. 1 A drawing showing Fragment 1 (F1), Fragment 2 (F2) and Fragment 3 (F3) used for cloning of the transcriptional regulatory region of human CYP1A1 and CYP1A2.

The present invention relates to an expression vector constituted so as to contain a region neighboring CYP1A1 as a transcriptional regulatory region, to reflect CYP1A2 induction by a drug, a host cell to which the expression vector is transfected, and a method for examining CYP1A2 induction by a test drug, using the host cell.

The present invention further relates to an expression vector constituted so that a reporter gene should be transcribed from a DNA comprising a region neighboring CYP1A1 in a reverse direction to reflect CYP1A1 and CYP1A2 induction by a drug simultaneously, a host cell to which the expression vector is transfected, and a method for examining CYP1A1 and CYP1A2 induction by a test drug, using the host cell.

Hereafter, 1. the method for constructing the expression vector, 2. the method for transfecting the expression vector into a host, and 3. the method for examining CYP1A1 and CYP1A2 induction by a drug, using the host cell will be explained.

1. Method for Constructing Expression Vector

The nucleotide sequence of the intergenic region between the CYP1A1 and CYP1A2 genes can be obtained from Gen-Bank Acc. No. AF253322. Moreover, a DNA comprising the region between the CYP1A1 and CYP1A2 genes can be obtained from a BAC clone (Genome Systems, BAC clone number: RP11-195A1 or RP11-414J4), or a human genome DNA (Novagen, catalog number: 69237; BD Bioscience, Catalog number: 636401).

The procedures described below can be performed according to methods described in an appropriate manual, for example, Molecular Cloning: A Laboratory Manual, Cold Spring Harbor, N.Y., and so forth.

By operably linking a reporter gene to a DNA comprising a region neighboring CYP1A1 on the side linked to the CYP1A2 gene (3' end side in SEQ ID NO: 1), an expression vector which reflects expression of CYP1A2 can be prepared. The reporter gene is a gene coding for a reporter gene, and means a gene of which expression amount can be measured by direct or indirect measurement of expression level of the reporter gene. Examples of the reporter gene include secreted alkaline phosphatase gene (GenBank #U89937), firefly luciferase gene (GenBank #U47295), chloramphenicol acetyltransferase gene (GenBank #U57024) and so forth, but not limited to them.

The expression "to be operably linked" means to be ligated in such a manner that expression of the reporter gene should be regulated by a DNA ligated.

As the DNA comprising a region neighboring CYP1A1, the whole region between the CYP1A1 and CYP1A2 genes may be used, and this region can be obtained by PCR using the aforementioned BAC clone as a template and primers designed on the basis of the information of the nucleotide sequence registered at GenBank. This region has a length of 20 kbp or more, and thus if it is difficult to amplify the whole region by PCR of 1 time, the whole region can be obtained by ligating the PCR products using the restriction enzyme cleavage sites, which are amplified as the regions between suitable restriction enzyme cleavage sites in this region by PCR on the basis of the information on the nucleotide sequence registered at GenBank.

Figure 2:
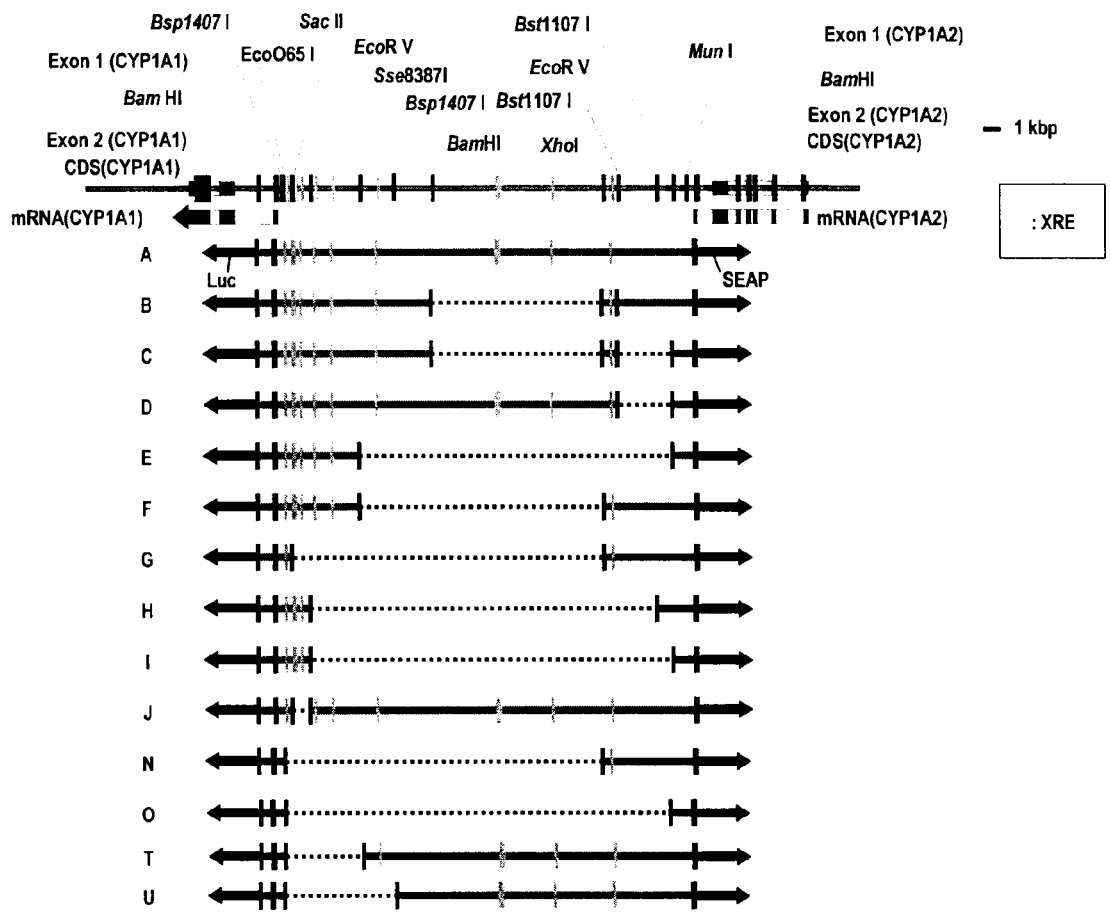
FIG. 2 A drawing showing the deleted regions of the reporter vectors B to J in which a part of the transcriptional regulatory region of human CYP1A1 and CYP1A2 was deleted.

Further, as shown in FIG. 2, a large number of XREs (xenobiotic responsive elements) are distributed between the CYP1A1 gene and the CYP1A2 gene. By referring to this distribution, appropriate transcriptional regulatory regions can be chosen and combined, and the region prepared can be used as a transcriptional regulatory region of the expression vector. In particular, the transcriptional regulatory region preferably contains the region of the nucleotide sequence of the nucleotide numbers 1925 to 2867 (preferably 1535 to 2866, more preferably 1 to 2867) in SEQ ID NO: 1, and it is preferable to select an appropriate region according to what kind of drug should be examined and ligate the selected region to the aforementioned region. The XRE referred to here is a sequence represented as tngcgtg (n is a, g, t or c). Further, this n is preferably t or c. Further, it is also possible to use a region comprising the nucleotide sequence of the nucleotide numbers 5659 to 24448 in SEQ ID NO: 1.

The transcriptional regulatory region containing XRE preferably comprises, for example, any of the transcriptional regulatory regions neighboring CYP1A1 mentioned below.
(1) A region consisting of the nucleotide sequence of the nucleotide numbers 1242 to 2866 in SEQ ID NO: 1.
(2) A region consisting of the nucleotide sequence of the nucleotide numbers 1 to 2866 in SEQ ID NO: 1.
(3) A region consisting of the nucleotide sequence of the nucleotide numbers 1 to 5658 in SEQ ID NO: 1.
(4) A region consisting of the nucleotide sequence of the nucleotide numbers 1 to 9690 in SEQ ID NO: 1.

(5) A region consisting of the nucleotide sequence of the nucleotide numbers 1 to 19986 in SEQ ID NO: 1.
(6) A region consisting of the nucleotide sequence of the nucleotide numbers 1925 to 6117 in SEQ ID NO: 1.
(7) A region consisting of the nucleotide sequence of the nucleotide numbers 1925 to 24448 in SEQ ID NO: 1.
(8) A region consisting of a nucleotide sequence comprising a nucleotide sequence of the nucleotide numbers 1 to 5658 in SEQ ID NO: 1 including deletion of any of the nucleotide sequence of the nucleotide numbers 1535 to 1541, the nucleotide sequence of the nucleotide numbers 1930 to 1936, the nucleotide sequence of the nucleotide numbers 2018 to 2024, the nucleotide sequence of the nucleotide numbers 2093 to 2099, and the nucleotide sequence of the nucleotide numbers 2411 to 2417.
(9) A region consisting of the nucleotide sequence of the nucleotide numbers 5659 to 24448 in SEQ ID NO: 1.

As shown in Examples 4 and 5, only with a transcriptional regulatory region neighboring CYP1A2, induction by a drug cannot be observed even when the transcription of the reporter gene can be caused, and in order to reflect such induction by a drug, any of these regions neighboring CYP1A1 is required. The term "region neighboring CYP1A1" used here means a 5' upstream region of the CYP1A1 gene (downstream from the CYP1A1 gene in SEQ ID NO: 1, since the CYP1A1 gene is transcribed in the reverse direction in SEQ ID NO: 1) of 10 kb, preferably 6 kb, more preferably 3 kb.

Depending on the case, it is also allowed to use a still larger region, for example, a region consisting of the nucleotide sequence of the nucleotide numbers 1 to 19946 in SEQ ID NO: 1.

Further, the reporter vector which enables evaluation of CYP1A2 induction by a drug preferably comprises, for example, any of the transcriptional regulatory regions neighboring CYP1A2 mentioned below, in addition to the regions mentioned above. The transcriptional regulatory region neighboring CYP1A2 may partially or fully overlap the aforementioned transcriptional regulatory region neighboring CYP1A1.
(10) A region consisting of the nucleotide sequence nucleotide sequence of the nucleotide numbers 23697 to 24448 in SEQ ID NO: 1.
(11) A region consisting of the nucleotide sequence of the nucleotide numbers 23030 to 24448 in SEQ ID NO: 1.
(12) A region consisting of the nucleotide sequence of the nucleotide numbers 22167 to 24448 in SEQ ID NO: 1.
(13) A region consisting of the nucleotide sequence of the nucleotide numbers 19134 to 24448 in SEQ ID NO: 1.
(14) A region consisting of the nucleotide sequence of the nucleotide numbers 1925 to 24448 in SEQ ID NO: 1.
(15) A region consisting of a nucleotide sequence of a DNA hybridizable with a DNA comprising a nucleotide sequence complementary to the nucleotide sequence of the nucleotide numbers 19134 to 24448 in SEQ ID NO: 1 under a stringent condition.

The present invention is based on the finding that, for the evaluation of CYP1A2 induction by a drug, it is required for the expression vector to include the nucleotide sequence of the nucleotide numbers 1925 to 2867 (preferably 1535 to 2866, more preferably 1 to 2867) in SEQ ID NO: 1 in which XREs densely exist (expression vectors A, B, C, D, E, F, H and I in FIG. 2), and if the expression vector does not contain such a region (expression vectors G, J, N and O in FIG. 2), the induction ability is markedly decreased. Therefore, expression vectors comprising a transcriptional regulatory sequence having the nucleotide sequence of the nucleotide numbers 1925 to 2867 (preferably 1535 to 2866) in SEQ ID NO: 1 or a similar sequence and showing increase in the expression of a reporter gene which is operably linked at the 3' end in the presence of a drug which induces CYP1A2 are all fall within the scope of the present invention.

According to the present invention, although the transcriptional regulatory sequence is required to have a region in which XREs are adjacently disposed, it may be appropriately shortened for ease of handling, and it may be a transcriptional regulatory sequence having a length of, for example, 25 kb or shorter, 20 kb or shorter, 15 kb or shorter, or 10 kb or shorter.

A preferred example of the transcriptional regulatory region comprising such a similar sequence is a DNA having a nucleotide sequence of the nucleotide numbers 1925 to 2866 (preferably 1535 to 2866, more preferably 1 to 28286667) in SEQ ID NO: 1 including deletion, substitution and/or addition of one or plural nucleotides and showing increase in the expression of a reporter gene which is operably linked at the 3' end in the presence of a drug which induces CYP1A2. The DNA preferably increases the expression of a reporter gene which is operably linked at the 5' end in the presence of a drug which induces CYP1A1. Although the number meant by the expression "two or more" is not particularly limited, it is 2 to 100, preferably 2 to 50, 2 to 20, or 2 to 10, more preferably 2 to 7. As shown in Example 7 of this specification, even if a part of the XRE regions was deleted, which are considered to be most important for the transcriptional regulation, the activity of a drug for inducing the expression was maintained. Therefore, expression vectors comprising a transcriptional regulatory region having a nucleotide sequence of the nucleotide sequence of the nucleotide numbers 1925 to 2866 (preferably 1535 to 2866, more preferably 1 to 2866) in SEQ ID NO: 1 including a mutation fall within the scope of the present invention, so long as they show increase in the expression in the presence of a drug. Mutations can be introduced by, for example, the site-directed mutagenesis method or the like.

Another example of the transcriptional regulatory region comprising such a similar sequence is a DNA comprising a nucleotide sequence showing a homology of 90% or more, preferably 95% or more, more preferably 97% or more, to the nucleotide sequence of the nucleotide numbers 1925 to 2866 (preferably 1535 to 2866, more preferably 1 to 2866) in SEQ ID NO: 1 and showing increase in expression of a reporter gene operably linked at the 3' end in the presence of a drug which induces CYP1A2. The DNA preferably increases the expression of a reporter gene which is operably linked at the 5' end in the presence of a drug which induces CYP1A1. The homology can be calculated by using homology searching sites on the Internet [for example, homology searching using FASTA, BLAST, PSI-BLAST, SSEARCH or the like is available on the web site of DNA Data Bank of Japan (DDBJ) [for example, the page of homogeny searching (Search and Analysis) on the web site of DNA Data Bank of Japan (DDBJ), http://www.ddbj.nig.ac.jp/E-mail/homology-j.html]. Further, search using BLAST can be performed on the web site of National Center for Biotechnology Information (NCBI) [for example, the page of BLAST on the homepage of NCBI, http://www.ncbi.nlm.nih.gov/BLAST/; Altschul, S. F. et al., J. Mol. Biol., 1990, 215(3):403-10; Altschul, S.F. & Gish, W., Meth. Enzymol., 1996, 266:460-480; Altschul, S. F. et al., Nucleic Acids Res., 1997, 25:3389-3402].

Another example of such a transcriptional regulatory region comprising a similar sequence is a DNA comprising a DNA hybridizable with a DNA comprising the nucleotide sequence of the nucleotide numbers 1925 to 2866 (preferably 1535 to 2866, more preferably 1 to 2866) in SEQ ID NO: 1 under a stringent condition and showing increase in expression of a reporter gene which is operably linked at the 3' end in the presence of a drug which induces CYP1A2. The DNA preferably increases expression of a reporter gene which is operably linked at the 5' end in the presence of a drug which induces CYP1A1.

Details of similar sequences of the nucleotide sequence of the nucleotide numbers 5659 to 9180 in SEQ ID NO: 1 are similar to those explained above for the nucleotide sequence of the nucleotide numbers 1925 to 2866 in SEQ ID NO: 1.

Further, the reporter vector for evaluating CYP1A2 induction by a drug preferably further comprises a transcriptional regulatory sequence having the nucleotide sequence of the nucleotide numbers 19134 to 24448 in SEQ ID NO: 1 or a similar transcriptional regulatory sequence. Details of similar sequences of this nucleotide sequence are also similar to those explained above for the nucleotide sequence of the nucleotide numbers 1925 to 2866 in SEQ ID NO: 1. A preferred example of such a similar sequence is a DNA hybridizable also with a DNA having the nucleotide sequence of the nucleotide numbers 19134 to 24448 (preferably 22167 to 24448, further preferably 23030 to 24448) in SEQ ID NO: 1 under a stringent condition.

Examples of the stringent hybridization condition referred to here include, for example, conditions of "2×SSC, 0.1% SDS, 50° C.", "2×SSC, 0.1% SDS, 42° C.", and "1×SSC, 0.1% SDS, 37° C.", and examples of more stringent condition include conditions of "2×SSC, 0.1% SDS, 65° C.", "0.5× SSC, 0.1% SDS, 42° C.", and "0.2×SSC, 0.1% SDS, 65° C.". More specifically, as a method of using Rapid-hyb buffer (Amersham Life Science), hybridization can be carried out by performing pre-hybridization at 68° C. for 30 minutes or more, then adding a probe, maintaining the system at 68° C. for 1 hour or more to form hybrids, then washing 3 times in 2×SSC and 0.1% SDS at room temperature for 20 minutes for each time, further washing 3 times in 1×SSC and 0.1% SDS at 37° C. for 20 minutes for each time, and finally washing twice in 1×SSC and 0.1% SDS at 50° C. for 20 minutes for each time. In addition, hybridization may be attained by, for example, performing pre-hybridization in ExpressHyb Hybridization Solution (CLONTECH) at 55° C. for 30 minutes or more, adding a labeled probe, incubating at 37 to 55° C. for 1 hour or more, washing 3 times in 2×SSC and 0.1% SDS at room temperature for 20 minutes for each time, and washing once in 1×SSC and 0.1% SDS at 37° C. for 20 minutes. By using higher temperatures for the pre-hybridization, hybridization and second washing (for example, 60° C., 68° C. etc.) in the aforementioned methods, a more stringent condition can be attained. Those skilled in the art can determine the conditions by considering other hybridization conditions such as probe concentration, length of probe, nucleotide sequence of probe and reaction time, in addition to the salt concentrations of the buffer and temperature. For the method of hybridization, Molecular Cloning: A Laboratory Manual 2nd ed. (Cold Spring Harbor Press (1989)); Current Protocols in Molecular Biology (John Wiley & Sons (1987-1997)); DNA Cloning 1: Core Techniques, A Practical Approach 2nd ed. (Oxford University (1995)), and so forth can be referred to as experimental manuals.

Such a transcriptional regulatory region comprising the nucleotide sequence of the nucleotide numbers 1925 to 2866 (preferably 1535 to 2866, more preferably 1 to 2866) in SEQ ID NO: 1 or a similar sequence can be obtained by performing PCR amplification using the aforementioned BAC clone as a template and primers designed on the basis of the information on the nucleotide sequence of GenBank and appropriately combining the obtained clones or modifying the nucleotide sequence according to a known method.

Preferred examples of the transcriptional regulatory sequence of the present invention include sequences comprising the following nucleotide sequences.

Figure 4:
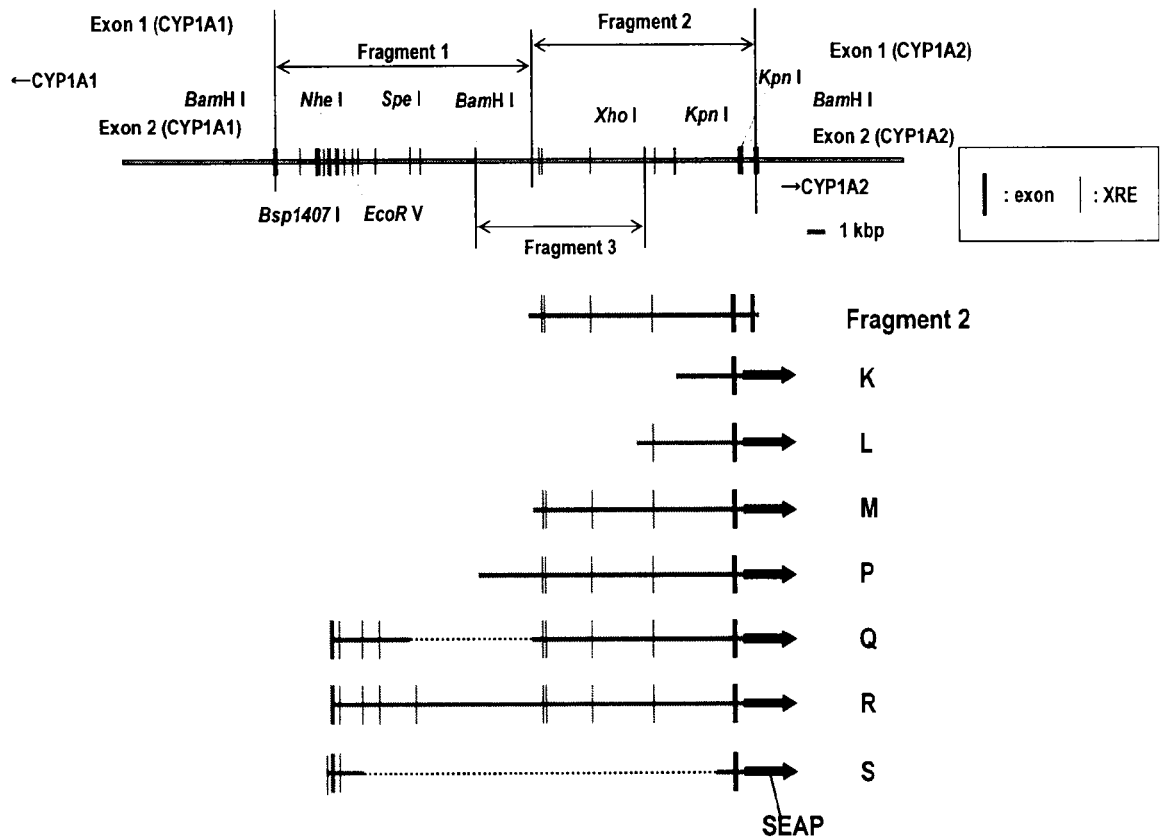
FIG. 4 A drawing showing the deleted regions of the reporter vectors K to M and P to S in which a part of the transcriptional regulatory region of human CYP1A1 and CYP1A2 was deleted.

(1) A sequence consisting of the nucleotide sequence of the nucleotide numbers 1242 to 2866 and the nucleotide sequence of the nucleotide numbers 23697 to 24448 in SEQ ID NO: 1 (expression vector S in FIG. 4)

(2) A sequence comprising the nucleotide sequence of the nucleotide numbers 1 to 2866 and the nucleotide sequence of the nucleotide numbers 23030 to 24448 in SEQ ID NO: 1 ligated to each other (expression vector I in FIG. 2)

(3) A sequence comprising the nucleotide sequence of the nucleotide numbers 1 to 2866 and the nucleotide sequence of the nucleotide numbers 22167 to 24448 in SEQ ID NO: 1 ligated to each other (expression vector H in FIG. 2).

(4) A sequence comprising the nucleotide sequence of the nucleotide numbers 1 to 5658 and the nucleotide sequence of the nucleotide numbers 23030 to 24448 in SEQ ID NO: 1 ligated to each other (expression vector E in FIG. 2).

(5) A sequence comprising the nucleotide sequence of the nucleotide numbers 1 to 5658 and the nucleotide sequence of the nucleotide numbers 19134 to 24448 in SEQ ID NO: 1 ligated to each other (expression vector F in FIG. 2)

(6) A sequence comprising the nucleotide sequence of the nucleotide numbers 1 to 9690 and the nucleotide sequence of the nucleotide numbers 19134 to 24448 in SEQ ID NO: 1 ligated to each other (expression vector B in FIG. 2).

(7) A sequence comprising the nucleotide sequence of the nucleotide numbers 1 to 19946 and the nucleotide sequence of the nucleotide numbers 23030 to 24448 in SEQ ID NO: 1 ligated to each other (expression vector D in FIG. 2).

(8) A sequence consisting of the nucleotide sequence of the nucleotide numbers 1 to 24448 in SEQ ID NO: 1 (expression vector A in FIG. 2)

(9) A sequence comprising the nucleotide sequence of the nucleotide numbers 1925 to 6117 and the nucleotide sequence of the nucleotide numbers 19134 to 24448 in SEQ ID NO: 1 ligated to each other (expression vector Q in FIG. 4).

(10) A sequence consisting of the nucleotide sequence of the nucleotide numbers 1925 to 24448 in SEQ ID NO: 1 (expression vector R in FIG. 4).

(11) A sequence comprising a nucleotide sequence of the nucleotide numbers 1 to 5658 in SEQ ID NO: 1 including deletion of any of the nucleotide sequence of the nucleotide numbers 1535 to 1541 (E1), the nucleotide sequence of the nucleotide numbers 1930 to 1936 (E2), the nucleotide sequence of the nucleotide numbers 2018 to 2024 (E3), the nucleotide sequence of the nucleotide numbers 2093 to 2099 (E4) and the nucleotide sequence of the nucleotide numbers 2411 to 2417 (E5), and the nucleotide sequence of the nucleotide numbers 23030 to 24448 ligated to each other.

(12) A sequence comprising the nucleotide sequence of the nucleotide numbers 1 to 1241 and the nucleotide sequence of the nucleotide numbers 5659 to 24448 in SEQ ID NO: 1 ligated to each other (expression vector T in FIG. 2).

Whether the prepared expression vector is usable as a reporter system reflecting the CYP1A2 induction can be verified by determining whether the expression of the reporter gene from the expression vector is enhanced by a drug known to induce CYP1A2 such as 3-methylcholanthrene or p-naphthoflavone.

The DNA comprising a region neighboring CYP1A1 may be further operably linked to a reporter gene at the end on the side to be linked to the CYP1A1 gene (5' end of SEQ ID NO: 1) in addition to the end on the side to be linked to the CYP1A2 gene (3' end of SEQ ID NO: 1). By linking reporter genes on both sides, an expression vector can reflect an expression of both the CYP1A1 and CYP1A2 genes. The reporter gene linked on the side to be linked to the CYP1A1 gene is preferably different from the reporter gene linked on the side linked to the CYP1A2 gene, so that expressions of them can be independently measured.

By using the reporter system in which different reporter genes are linked on both sides of a DNA comprising a region neighboring CYP1A1, inductions of CYP1A1 and CYP1A2 by a drug can be simultaneously measured, and thus labor for experiments can be markedly reduced.

2. Method for Transfection into Host

A host cell is transfected with the constructed expression vector. Many cell lines have already been established as host cell lines, and various transfection methods suitable for those host cell lines have also been established. As a host cell of the reporter system of the present invention, any of these known host cell lines may be used, and transfection can be efficiently performed by those skilled in the art by employing an appropriate transfection method suitable for a selected host. Examples include, for example, the lipofectamine method (GIBCO BRL), but not limited to this method. In addition, the calcium phosphate precipitation method, nuclear microinjection, protoplast fusion, DEAE-dextran method, cell fusion, electroporation, method of using FuGENE6 reagent (Roche) and so forth are also known. For the details of the transfection of mammalian cells, literatures such as Keown et al., Methods in Enzymol., 185:527-537 (1990); Mansour et al., Nature, 336:348-352 (1988) and so forth can be referred to.

A mammalian cell line can be used, and many kinds of cells such as HepG2, HuH-7, Hela, COS-1 and human immortalized hepatocyte are known. These cells can be used as a host cell of the reporter system. It is preferable to use a cell line derived from a hepatocyte, and HepG2, HuH-7 and human immortalized hepatocyte are still more preferred. As the host cell, a cell in which the transfected expression vector is transiently expressed may also be used, or a cell line which is made to permanently harbor the expression vector by transfection of the expression vector to which a selection marker is introduced and selection with a drug corresponding to the marker may also be used.

3. Test Method for CYP1A2 or CYP1A1 and CYP1A2 Induction

A test for CYP1A2 induction can be performed with the following steps.

(1) A host cell to which the expression vector is transfected is cultured in the presence or absence of a drug for appropriate time.

(2) Expression level of the reporter gene is measured by a method corresponding to the introduced reporter gene. For example, the expression level of the reporter gene is measured by measuring enzymatic activity in the culture supernatant if the reporter gene encoded by the reporter gene is a secreted enzyme, by measuring enzymatic activity of cell extract if it is an enzyme to be intracellularly expressed, or by measuring fluorescence if it is a molecule which emits fluorescence.

(3) The expression level observed in the presence and absence of the drug are compared, and if the expression level of the reporter gene increases in the presence of the drug, it is determined that the drug has an ability to induce CYP1A2.

Further, if a host to which the expression vector ligated with the reporter gene also on the side to be linked to CYP1A1 in addition to the side to be linked to CYP1A2 is introduced is used, it becomes possible to simultaneously evaluate ability to induce CYP1A1 and ability to induce CYP1A2.

With the reporter system of the present invention, for example, induction by a drug which causes the induction by binding with an aryl hydrocarbon receptor and then binding with XRE, an environmental hormone (Denison, M. S et al., Annual Review of Pharmacology & Toxicology, 43:p. 309-34, 2003), or the like can be evaluated.

Example 1

1. Cloning of Transcriptional Regulatory Region Fragment of Human CYP1A1 and CYP1A2 Genes A DNA comprising the transcriptional regulatory region of human CYP1A1 and CYP1A2 genes was amplified as three fragments (Fragments 1 to 3) divided in the upstream regions of the CYP1A1 and CYP1A2 genes by PCR using the BAC clone (Genome Systems) as a template and LA Taq (TaKaRa) (FIG. 1). The used primers are as follows, which were designed on the basis of the sequence of NCBI DB accession No. AF253322.

```
Fragment 1:
Forward primer
                                                          (SEQ ID NO: 2)
5'-GCGGTCGACGGCCGGCCGGATCTCATTCTTTTTACAGCTGAATAGCACTCC-3'

Reverse primer
                                                          (SEQ ID NO: 3)
5'-GCGGAATTCATCTTGGAGGTGGCTGCTGAGAGAAGGTGC-3'

Fragment 2:
Forward primer
                                                          (SEQ ID NO: 4)
5'-GCGCTCGAGAGAATACCAGGCAGAAGATGGCAGAGG-3'

Reverse primer
                                                          (SEQ ID NO: 5)
5'-GCGACGCGTGGCCGGCCATATAGTGCATATACACAATGGAGTGCTATTCAGCTGT-3'

Fragment 3:
Forward primer
                                                          (SEQ ID NO: 6)
5'-TCCCAGCTACTCGAGAGGTTGACACACAAGAA-3'

Reverse primer
                                                          (SEQ ID NO: 7)
5'-CGACGCGTCCCGCTCGAGGATCCTCATAAATGGTTTAGCACCATCC-3'
```

Each of the obtained PCR products (referred to as F1, F2 and F3, respectively) was subcloned into pCR-XL-TOPO (Invitrogen).

2. Construction of Reporter Vector pGL3-Basic (Promega) and pSEAP2-Basic (CLONTECH) (referred to as V1 and V2, respectively) were used to construct a reporter vector according to the following procedures. The clones obtained in each step were subjected to a restriction enzyme treatment and then agarose gel electrophoresis to confirm that they were objective vectors.
(a) F1 was digested with BamHI to obtain about 10-kbp fragment, and the fragment was inserted into V1 at the BglII site.
(b) F2 was digested with XhoI and BamHI to obtain about 5.3-kbp fragment, and the fragment was inserted into V2 between the XhoI and BglII sites.
(c) The vector obtained in (a) was digested with XhoI and SalI to obtain about 12-kbp fragment, and the fragment was inserted into the vector obtained in (b) at the XhoI site.
(d) F3 was digested with XhoI to obtain about 9.5-kbp fragment, and the fragment was inserted into the vector obtained in (c) at the XhoI site.

3. Preparation of Reporter Vectors Deleted a Part of Transcriptional Regulatory Region of Human CYP1A1 and CYP1A2

As shown in FIG. 2, the reporter vectors B to J, N, O, T and U deleted a part of the transcriptional regulatory region of human CYP1A1 and CYP1A2 were prepared.
A: It was the vector prepared in 2 mentioned above, which did not include deletion.
B: It was prepared by the following procedures.
(e) F1 was digested with BamHI to obtain about 10-kbp fragment, and the fragment was inserted into V1 at the BglII site.
(f) F2 was digested XhoI and BamHI to obtain about 5.3-kbp fragment, and the fragment was inserted into V2 between the XhoI and BglII sites.
(g) The vector obtained in (e) was digested with XhoI and SalI to obtain about 12-kbp fragment, and the fragment was inserted into the vector obtained in (f) at the XhoI site.
C: B was digested with Bst1107I and ligated itself.
D: B was digested with Bst1107I to obtain about 21-kbp and 6.9-kbp fragments. After purifying the fragments, the 21-kbp fragment was de-phosphorylated and ligated to the 6.9-kbp fragment.
E: B was digested with Sse8387I and Bst1107I to obtain about 13.7-kbp fragment. After purifying the fragment, the 13.7-kbp fragment was blunt-ended and ligated itself.
F: B was digested with Sse8387I and XhoI to obtain about 17.6-kbp fragment. After purifying the fragment, the fragment was blunt-ended and ligated itself.
G: It was prepared by the following procedures.
(h) B was digested with NheI to obtain about 4-kbp fragment.
(i) The vector obtained in (b) was digested with NheI, and the fragment obtained in (h) was inserted.
H: B was digested with EcoRV and ligated itself.
I: B was digested with Bst1107I to obtain about 18.5-kbp fragment, and the fragment was digested with EcoRV and ligated itself.
J: It was prepared by the following procedures.
(j) B was digested with XhoI and SalI to obtain about 14.5-kbp fragment. After purifying the fragment, the product was self-ligated.
(k) The vector obtained in (j) was digested with SacII and EcoRV to obtain about 13.2-kbp fragment, and the resultant fragment was blunt-ended, and the product was ligated itself.
(l) The vector obtained in (k) was digested with Sse8387I and MluI to obtain about 6.3-kbp fragment. After purifying the fragment, the fragment was inserted into A between the Sse8387I and MluI sites.

N: F was digested with HindIII to obtain about 11-kbp fragment. The fragment was inserted into pRL-SV40 (Promega) at the HindIII site, then the pRL-SV40 was digested with EcoO65I and XhoI and subject to blunt-ending treatment, and then the product was self-ligated. The product was digested with HindIII to obtain the insert, and the insert was ligated with V3.
O: H was digested with HindIII to obtain about 5-kbp and 6-kbp fragments. The 6-kbp fragment was inserted into V1 at the HindIiI site, then the V1 was digested with EcoO65I and Bst1107I and subject to blunt-ending treatment, and then the product was self-ligated. The product was digested with HindIII to obtain the insert, and the insert was ligated with about 5-kbp fragment obtained by HindIII digestion of H (referred to as V3).
T: It was prepared by the following procedures.
(t1) F1 was digested with BamHI to obtain about 9.7-kb fragment, and the fragment was inserted into V2 at the BglII site.
(t2) The (t1) product was digested with HindIII to obtain about 9.1-kb fragment, and the fragment was inserted into V2 at the HindIII site.
(t3) The (t2) product was digested with Sse8387I and Bsp1407I to obtain about 9.3-kb fragment, and the fragment was subjected to a blunt-ending treatment, and self-ligated.
(t4) F1 was digested with BamHI to obtain about 9.7-kb fragment, and the fragment was inserted into V1 at the BglII site. This product was digested with HindIII to obtain about 5.5-kb fragment.
(t5) The (t3) product was digested with HindIII and BamHI to obtain about 4.6-kb fragment. This fragment and the
(t4) product were ligated.
(t6) The (t5) product was digested with XhoI and SalI and inserted into L at the XhoI site.
(t7) F3 was digested with XhoI to obtain about 9.5-kb fragment, and the fragment was inserted into the (t6) product at the XhoI site.
U: It was prepared by the following procedures.
(u1) The (t1) product was digested with Bsp1407I, and the obtained 6.4-kb fragment was self-ligated. The product was digested with MluI and HindIII to obtain about 1.8-kb fragment. This fragment was inserted into V1 between MluI and HindIII sites.
(u2) L was digested with XhoI and SalI to obtain about 7.1-kb fragment. This fragment was inserted into the (u1) product at the XhoI site.
(u3) F3 was digested with XhoI to obtain about 9.5-kb fragment, and the fragment was inserted into the (u2) product at the XhoI site.

The clones obtained in each step were subjected to a restriction enzyme treatment and then agarose gel electrophoresis to confirm that they were objective vectors.

4. Reporter Assay Using Expression Vectors A to J, N, O, T and U

Each of the obtained reporter vector comprising the transcriptional regulatory region of human CYP1A1 and CYP1A2 and reporter vectors comprising the transcriptional regulatory region partially deleted was transiently expressed in HepG2 cells (purchased from RIKEN) by using a transfection reagent (FuGene6, Roche), and 40 hours after the addition of a drug dissolved in DMSO or DMSO alone, the activity of a secreted alkaline phosphatase (SEAP), which reflects CYP1A2, and the activity of a luciferase (Luc), which reflects CYP1A1, were measured. LumiPhos 530 (Lumigen Inc.) was used as a substrate for the measurement of the SEAP activity. The Luc activity was measured by using Luciferase Assay System (Promega) (FIG. 3).

Figure 3:
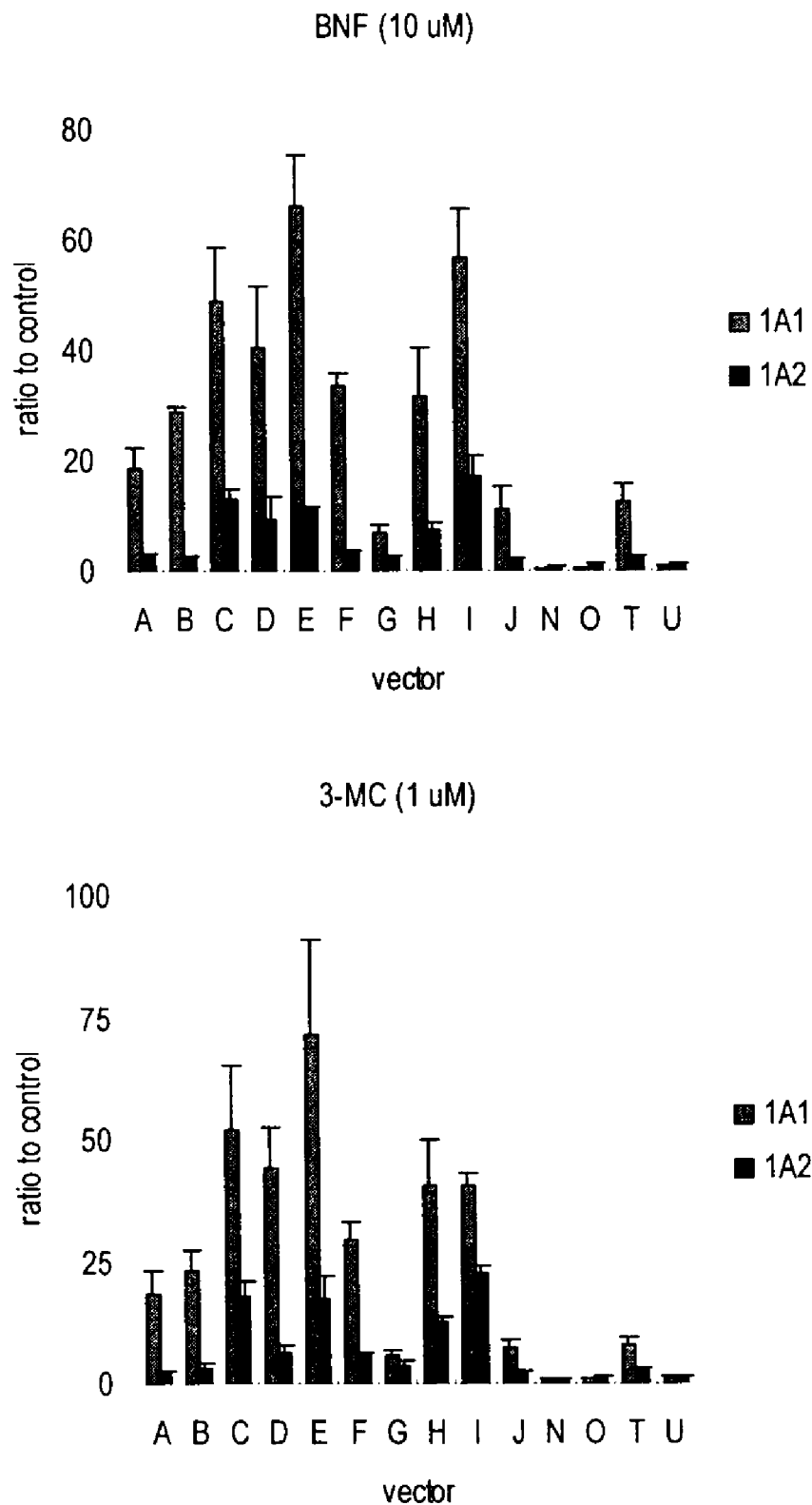
FIG. 3 Graphs showing how many folds the expression of the reporter vectors A to J, N, O, T and U was increased by the addition of 3-methylcholanthrene (3-MC, 1 μM, upper graph) or β-naphthoflavone (BNF, 10 μM, lower graph).

In FIG. 3, how many folds the reporter activity increased when each drug was added compared with the case where only DMSO was added is shown. When 3-methylcholanthrene (3-MC, 1 µM) or β-naphthoflavone (BNF, 10 µM), which are known to induce CYP1A1 and CYP1A2, was added, the increase in the SEAP activity and Luc activity was observed as compared with the group where DMSO alone was added.

In particular, with the reporter vectors comprising the region of the nucleotide sequence of the nucleotide numbers 1535 to 2867 in SEQ ID NO: 1 in which XREs densely existed, intense enhancement of the expression by 3-MC and BNF was observed as shown in FIG. 2, and thus it was expected that this region was involved in the induction of CYP1A1 and CYP1A2 by a drug.

5. Preparation of CYP1A2 Reporter Vectors and Reporter Assay

Reporter vectors K to M and P to S, which were considered to comprise the transcriptional regulatory region of human CYP1A2 and shown in FIG. 4, were prepared.
K: It was prepared by the following procedures.
(m) F2 was digested with KpnI to obtain about 3.2-kbp fragment.
(n) The (m) product was inserted into V2 at KpnI site.
L: It was prepared by the following procedures.
(o) F2 was digested with XhoI and BamHI to obtain about 5.3-kbp fragment.
(p) The (o) product was inserted into V2 at the XhoI/BglII sites.
M: It was prepared by the following procedures.
(q) F2 was digested with MluI and HindIII to obtain about 3-kbp fragment, and the fragment was inserted into V2 between the MluI and HindIII sites.
(r) V2 was digested with HindIII to obtain about 9-kbp fragment, and the fragment was inserted into the (q) product at the HindIII site.
P: It was prepared by the following procedure.
(s) F3 was digested with XhoI to obtain about 9.5-kbp fragment, and the fragment was inserted into L between the XhoI sites.
Q: It was prepared by the following procedure.
(t) F1 was digested with NheI and SpeI to obtain about 4.2-kbp fragment, and the fragment was inserted into L between the NheI sites.
R: It was prepared by the following procedure.
(u) A was digested with NheI, and the product was self-ligated.
S: It was prepared by the following procedures.
(v) F1 was digested with Bsp1407I and EcoRV to obtain about 1.6-kb fragment, and the fragment was inserted into V2 at the Asp718I/NruI sites.
(w) K was digested with MunI and EcoRI to obtain about 790-bp fragment. This fragment was inserted into the (v) product at the EcoRI site.

The clones obtained in each step were subjected to a restriction enzyme treatment and then agarose gel electrophoresis to confirm that they were objective vectors.

Figure 5:
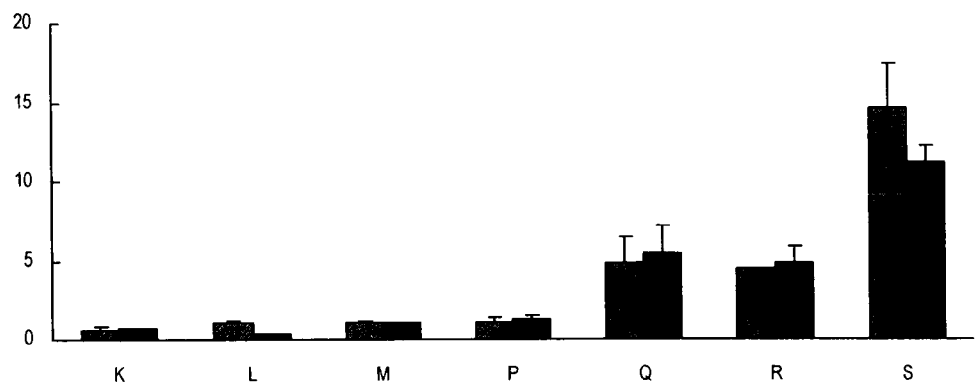
FIG. 5 A graph showing how many folds the expression of the reporter vectors K to M and P to S was increased by the addition of a compound.

In the same manner as that in 4, the expression vectors K to M and P to S obtained above were transiently expressed in HepG2 cells by using the gene transfer reagent, and 40 hours after the addition of a drug dissolved in DMSO or DMSO alone, activity of a secreted alkaline phosphatase (SEAP) was measured (FIG. 5).

In FIG. 5, how many folds the reporter activity increased when each drug was added compared with the case where only DMSO was added is shown. When the expression vector K, L or P was used, the reporter activity after addition of BNF or 3-MC was almost the same as that obtained with the addition of DMSO (1 fold), and elevation in the reporter activity was not observed. When the expression vector M was used, the reporter activity observed after addition of DMSO or an inducers were at the background level.

On the other hand, when the expression vector Q, R or S comprising the region neighboring CYP1A1 was used, 5- to 6-fold higher reporter activity was observed after the addition of BNF or 3-MC compared with the case where DMSO was added, and thus induction by a drug was observed.

As shown by the above results together with the results shown in FIG. 3, with a reporter vector comprising the region of the nucleotide sequence of the nucleotide numbers 1925 to 2866 in SEQ ID NO: 1 in which XREs densely existed, strong expression enhancement by 3-MC and BNF was observed, and thus it was expected that this region was involved in the induction of CYP1A2 by a drug.

With only the transcriptional regulatory region neighboring human CYP1A2, induction by a drug was not observed, although the transcription took place, or the transcription itself was not observed depending on the case (expression vector M). It was thus revealed that the region neighboring CYP1A1 was indispensable for reflection of the induction of CYP1A2 transcriptional activity by a drug.

6. Examination of Induction by Omeprazole Using Each of Expression Vectors A to J, N, O, T and U By using the reporters A to J, N, O, T and U, with which it was revealed in 4 that the induction was caused by 3-methylcholanthrene and β-naphthoflavone, it was examined whether the transcriptional induction of a reporter enzyme would be caused by omeprazole, which is also known to have the induction activity (FIG. 6).

In the same manner as that in 4, each of the expression vectors A to J, N, O, T and U was transiently expressed in HepG2 cells by using the transfection reagent, and 40 hours after the addition of a drug dissolved in DMSO or DMSO alone, activity of a secreted alkaline phosphatase (SEAP), which reflects CYP1A2, and activity of a luciferase (Luc), which reflects CYP1A1, were measured.

Figure 6:
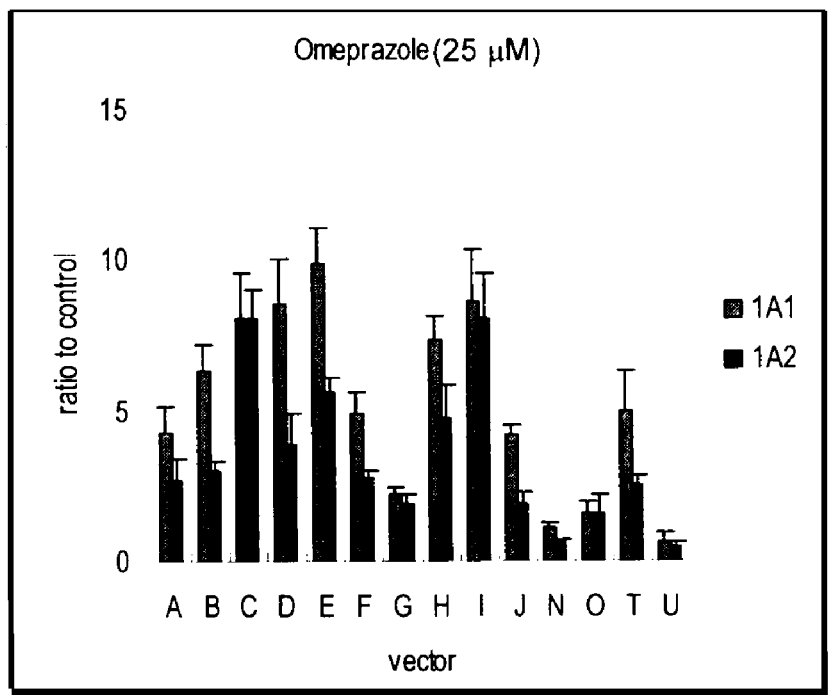
FIG. 6 A graph showing how many folds the expression of the reporter vectors A to J, N, O, T and U was increased by the addition of omeprazole.

In FIG. 6, how many folds the reporter activity increased when the drug was added compared with the case where only DMSO was added is shown. Induction of the reporter enzymes expression was also observed with omeprazole like 3-methylcholanthrene or β-naphthoflavone, and thus it was confirmed that the reporter system reflects the induction of CYP1A1 and CYP1A2 by a drug.

7. Preparation of Reporter Vectors Deleted Each XRE and Reporter Assay

From the reporter vector E, reporter vectors in which Each of five XREs (5'-TNGCGTG-3') in the reporter vector E was deleted from the one closer to the transcriptional initiation site of CYP1A1 gene were prepared by the site-directed mutagenesis, and they were designated as E1 to E5, respectively.

For the site-directed mutagenesis, the following DNAs were used as templates.
1) E1: DNA obtained by digesting E with SacII, allowing the product to cause self-ligation, further subjecting the product to KpnI digestion, and allowing the product to cause self-ligation.
2) E2 to E5: DNA obtained by digesting E with NheI, allowing the product to cause self-ligation, further subjecting the product to NdeI digestion, and allowing the product to cause self-ligation.

Further, the primers used are summarized in Table 1. In the parentheses in the table, the positions of these XREs in SEQ ID NO: 1 are indicated.

TABLE 1

```
E1     Forward  5'-CTGAGTCCCGGCAGAAGCGCTGCG-3'
(1535) primer   (SEQ ID NO: 8)
       Reverse  5'-CGCAGCGCTTCTGCCGGGACTCAG-3'
       primer   (SEQ ID NO: 9)

E2     Forward  5'-GCGTGCTAGCCGCCGGCGAC-3'
(1930) primer   (SEQ ID NO: 10)
       Reverse  5'-GTCGCCGGCGGCTAGCACGC-3'
       primer   (SEQ ID NO: 11)

E3     Forward  5'-GTGCCCAGGCGAGAAGGACCGGAG-3'
(2018) primer   (SEQ ID NO: 12)
       Reverse  5'-CTCCGGTCCTTCTCGCCTGGGCAC-3'
       primer   (SEQ ID NO: 13)

E4     Forward  5'-CGGGGGCTCGCAGTGGGGGAGGGAGTC-3'
(2093) primer   (SEQ ID NO: 14)
       Reverse  5'-GACTCCCTCCCCCCACTGCGAGCCCCCG-3'
       primer   (SEQ ID NO: 15)

E5     Forward  5'-CCAGGAAAAAAAAAGTTGTATCCTAGCTCAACCTGGCC-3'
(2411) primer   (SEQ ID NO: 16)
       Reverse  5'-GGCCAGGTTGAGCTAGGATACAACTTTTTTTTCCTGG-3'
       primer   (SEQ ID NO: 17)
```

Figure 7:
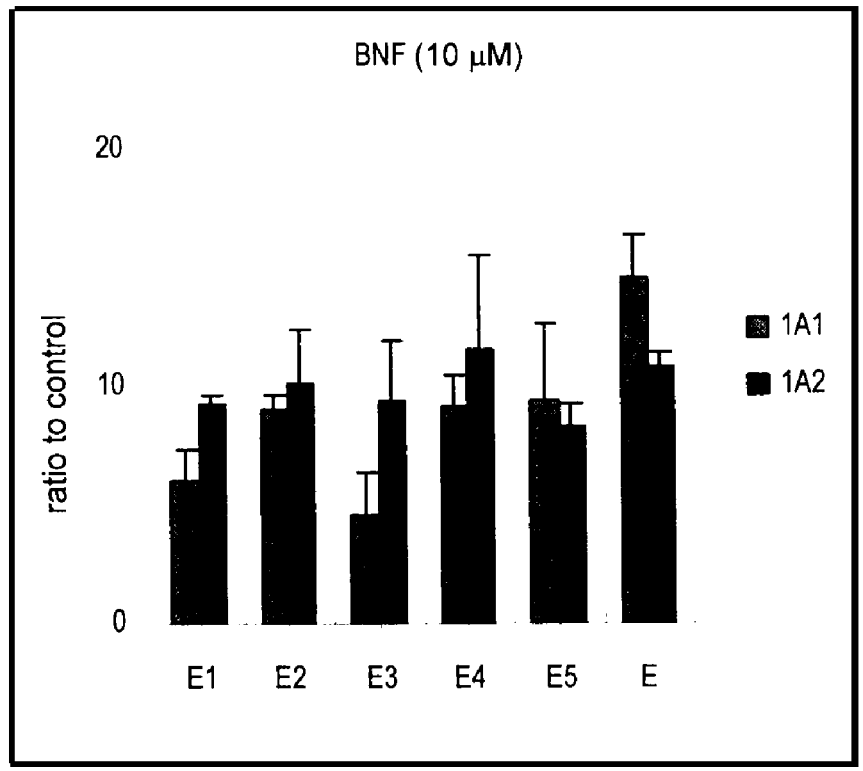
FIG. 7 A graph showing how many folds the expression of the reporter vectors E1 to E5 was increased by the addition of BNF.
Figure 8:
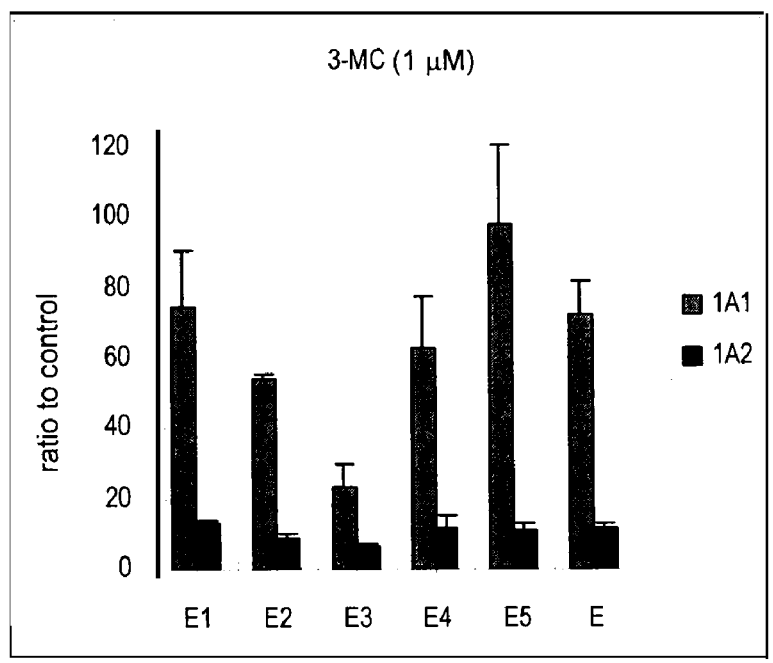
FIG. 8 A graph showing how many folds the expression of the reporter vectors E1 to E5 was increased by the addition of 3-MC.
Figure 9:
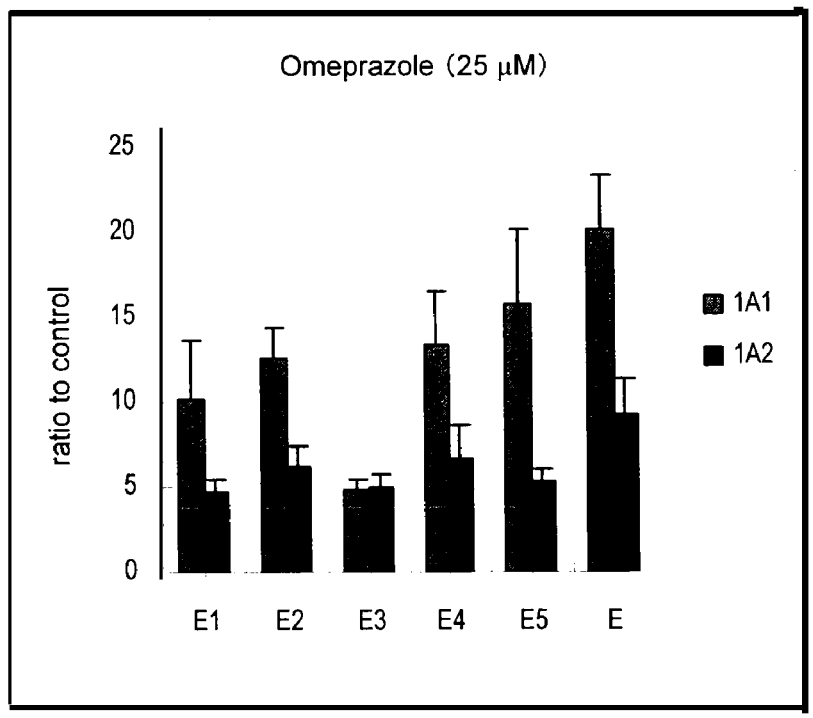
FIG. 9 A graph showing how many folds the expression of the reporter vectors E1 to E5 was increased by the addition of omeprazole.
Figure 10:
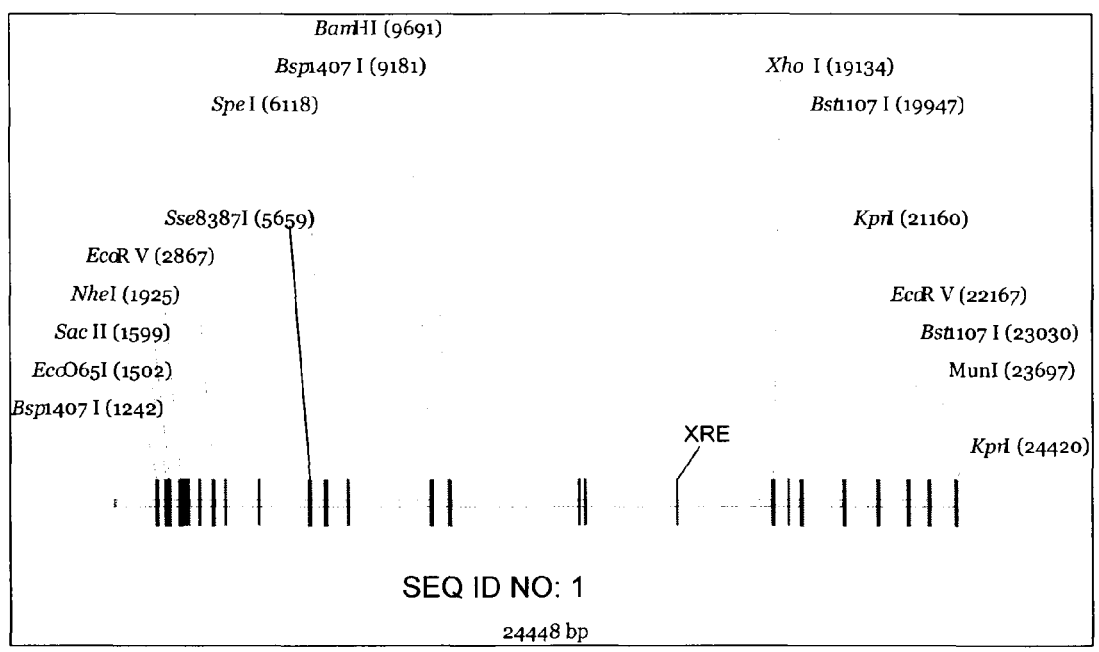
FIG. 10 A drawing showing cleavage sites of the restriction enzymes used for the preparation of the reporter vectors of the present invention.

A reporter assay was performed by using the obtained vectors. The results are shown in FIGS. 7 to 9. After addition of BNF, 3-MC or omeprazole, the reporter activities showed several folds to 10 or more folds higher than that observed after addition of DMSO, although E3 deleted the third XRE showed a slightly lower activity, and thus it was revealed that the ability to induce expression was maintained even if a part of XREs was deleted. It was considered to be necessary for the induction of expression by a drug that XREs should densely exist to some extent.

For the reporter vector M, for which result is shown in FIG. 5, increase in the reporter activity by addition of a drug was not observed, although it comprised four XREs on the CYP1A2 side (E9, E10, E11 and E12 in Table 2). Further, because the reporter activity did not significantly change for the reporter vectors E, H and I including deletion of these XREs, it is considered that these XREs are not necessarily important for the induction by a drug. The sequences of these XREs all corresponded to TGGCGTG or TAGCGTG.

On the other hand, XREs considered to play an important role for the induction of both the genes are E1 to E5, and all these sequences corresponded to TCGCGTG (E1, E4) or TTGCGTG (E2, E3, E5).

Further, in comparison of the reporter vectors T and U with reference to FIGS. 2 and 3, although the sequence of T did not comprise the region of the nucleotide numbers 1535 to 2866 in SEQ ID NO: 1 where XREs densely existed, it comprised XRE starting from 6642 (E8 in Table 2, TTGCGTG), and T showed strong enhancement of expression by 3-MC and BNF, whereas U of which sequence did not comprise E8 did not show the induction. Therefore, it was considered that XRE of E8 also played an important role for the induction by a drug.

From these facts, it was expected that one playing an important role for the induction of CYP1A1 and CYP1A2 was TCGCGTG or TTGCGTG.

TABLE 2

| Code | Sequence of XRE | Position in SEQ ID NO: 1 |
|---|---|---|
| E1 | TCGCGTG | 1353 |
| E2 | TTGCGTG | 1930 |
| E3 | TTGCGTG | 2018 |
| E4 | TCGCGTG | 2093 |
| E5 | TTGCGTG | 2411 |
| E6 | TGGCGTG | 3148 |
| E7 | TGGCGTG | 4106 |
| E8 | TTGCGTG | 6642 |
| E9 | TGGCGTG | 13245 |
| E10 | TGGCGTG | 13422 |
| E11 | TAGCGTG | 16099 |
| E12 | TGGCGTG | 19649 |

Industrial Applicability

According to the present invention, a reporter system reflecting induction of human CYP1A1 or CYP1A1 and CYP1A2 is established, and screening of drugs which induce them becomes easy.

What is claimed is:

1. An expression vector comprising a reporter gene operably linked to the 3' end of the nucleotide sequence of (C), (D), (E), (H), (I), (S) or (E1-E5):
   wherein (C) is a nucleotide sequence consisting of nucleotides 1 to 9690, 19134 to 19946, and 23030 to 24448 of SEQ ID NO:1;
   (D) is a nucleotide sequence consisting of nucleotides 1 to 19946 and 23030 to 24448 of SEQ ID NO:1;
   (E) is a nucleotide sequence consisting of nucleotides 1 to 5658 and 23030 to 24448 of SEQ ID NO:1;
   (H) is a nucleotide sequence consisting of nucleotides 1 to 2866 and 22167 to 24448 of SEQ ID NO:1;
   (I) is a nucleotide sequence consisting of nucleotides 1 to 2866 and 23030 to 24448 of SEQ ID NO:1;
   (S) is a nucleotide sequence consisting of nucleotides 1242 to 2866 and 23697 to 24448 of SEQ ID NO: 1; or
   (E1-E5) is a nucleotide sequence consisting of nucleotides 1 to 5658 and 23030 to 24448 of SEQ ID NO: 1 including a deletion of any of nucleotides 1535 to 1541, 1930 to 1936, 2018 to 2024, 2093 to 2099 and 2411 to 2417.

2. The expression vector according to claim 1, wherein the nucleotide sequence is
   (C) a nucleotide sequence consisting of nucleotides 1 to 9690, 19134 to 19946, and 23030 to 24448 of SEQ ID NO:1;
   (D) a nucleotide sequence consisting of nucleotides 1 to 19946 and 23030 to 24448 of SEQ ID NO:1;
   (E) a nucleotide sequence consisting of nucleotides 1 to 5658 and 23030 to 24448 of SEQ ID NO:1;
   (H) a nucleotide sequence consisting of nucleotides 1 to 2866 and 22167 to 24448 of SEQ ID NO:1; or
   (I) a nucleotide sequence consisting of nucleotides 1 to 2866 and 23030 to 24448 of SEQ ID NO: 1.

3. An isolated host cell into which the expression vector according to claim 1 is introduced.

4. A method for measuring ability of a test drug to induce CYP1A2, comprising (1) culturing the host cell according to claim 3 in the presence of the test drug, (2) measuring expression amount of the reporter gene, and (3) determining that the test drug has an ability to induce CYPIA2 gene, when the expression amount is affected as compared with the expression amount observed in the absence of the test drug.

5. The expression vector according to claim 1, wherein the nucleotide sequence is a nucleotide sequence which increases expression of a second reporter gene operably linked to the 5' end in the presence of a drug which induces CYP1A1 gene, and wherein said second reporter gene is different from the reporter gene that is linked to the 3' end.

6. An isolated host cell to which the expression vector according to claim 5 is introduced.

7. A method for measuring abilities of a test drug to induce CYP1A1 and CYP1A2 genes, comprising (1) culturing the host cell according to claim 6 in the presence of the test drug, (2) measuring expression amounts of the reporter genes, and (3) determining that the test drug has abilities to induce CYP1A1 and CYP1A2 genes, when the expression amounts are affected as compared with the expression amounts observed in the absence of the test drug.

8. The method according to claim 7, wherein the nucleotide sequence DNA is:
   (C) a nucleotide sequence consisting of nucleotides 1 to 9690, 19134 to 19946, and 23030 to 24448 of SEQ ID NO:1;
   (D) a nucleotide sequence consisting of nucleotides 1 to 19946 and 23030 to 24448 of SEQ ID NO:1;
   (E) a nucleotide sequence consisting of nucleotides 1 to 5658 and 23030 to 24448 of SEQ ID NO:1;
   (H) a nucleotide sequence consisting of nucleotides 1 to 2866 and 22167 to 24448 of SEQ ID NO:1; or
   (I) a nucleotide sequence consisting of nucleotides 1 to 2866 and 23030 to 24448 of SEQ ID NO:1.

* * * * *

```
                            SEQUENCE LISTING

<160> NUMBER OF SEQ ID NOS: 17

<210> SEQ ID NO 1
<211> LENGTH: 24448
<212> TYPE: DNA
<213> ORGANISM: Homo sapiens
<220> FEATURE:
<221> NAME/KEY: modified_base
<222> LOCATION: (1202)..(1202)
<223> OTHER INFORMATION: a, c, g, t, unknown or other
<220> FEATURE:
<221> NAME/KEY: modified_base
<222> LOCATION: (1205)..(1205)
<223> OTHER INFORMATION: a, c, g, t, unknown or other
<220> FEATURE:
<221> NAME/KEY: modified_base
<222> LOCATION: (1208)..(1208)
<223> OTHER INFORMATION: a, c, g, t, unknown or other
<220> FEATURE:
<221> NAME/KEY: modified_base
<222> LOCATION: (21955)..(21955)
<223> OTHER INFORMATION: a, c, g, t, unknown or other

<400> SEQUENCE: 1
gatccagagg gaagagaaaa cccagatctg ctgtgggaa cctgacagtc ttaccagtta      60
ggctccccac aggagaacct cacaagacag ggagatggat ggttcctacc acaagtatta     120
tagtggaggg aggcttcctg gagggctaa atatcaaagc acactagatc cctgagtcaa     180
caggggacag tgccaggctt tggtgtgcta tggtgtcccc ttctgcacag tgggtatccc     240
aaggacctgc agcctttgta agatggtagg aggccaaggg agatgtgact ggtgagtttt     300
tagggactgg tatttccagc tccctgcagt tggcaatctg tcaacctgat tgtctcccag     360
caaaggacaa agaagatggt caatgagata ggaaaggcct gggactcctg cacagatctg     420
cctctattgt cccagctgtc taggacatct cagcactgac aagccaccct taggagggta     480
aaatctgcca ggggtagctt cttaggctag ggcagggtac agctggtaag aacccagccc     540
accccctcca tccaccctgt ccacccaagg agaagcccct gtcatcagaa agcctgaggg     600
aggggctgca catattccag cctgccaggt ggccttgatg gggaagcccc agggtaggca     660
gggagacact cactagggga tggagctgga gcctgggtcc tgaagtcctg aatgagatgc     720
catctgtatc tagaggtctg gtaccagctg tgggaccatg ggcaagtcct cctcttcccc     780
tggcctcagt ttccccacta gggggctaga ctgcctggtc actaaaaaca ctctgagcct     840 cccttttttgg aggtgctaga caggtagcta cctaagaagt cctggaggca ccaaaatgtt     900
ccttttattg ggagagaaag ggcaagccag aagtccccca gcaactcacc tgaggtactg     960
agctgagctg ggaagggtgg actcttggag cctgggatca caaggatcag ggaaggttcc    1020
aaggaactgt caccttcagg gtgagggtga aggcactgcc acctttatag gcgggcttgt    1080
acgtgtggcc acgcctcctt ccctggagcg agctgagatg gagggagaag cagcctgaac    1140
cgggctggtc tctctgggat tggagagaaa ggtggcggag ggcggcgggg gtgggggtc    1200 gnctngtnca tgaacccact atgggacaca tctcggtgcc tgtacataga ggggtgaggg    1260
ctgggaacac ctggaagtcc caattccaag gcgtcccaag ggcagtgcag aacccagccg    1320
```

```
aggaggggc  ttgagggaga  agtcccagga  cagcccgaag  agagggtacg  ggaagctcca   1380
tcctggggcg  cggggactcc  tcttcgtcat  ttttgcaccc  actggaacgc  tgggcgtgca   1440
gatgcctccc  cagcgctaca  gcctaccagg  actcggcagg  cgggggcggg  gctgccccgt   1500
ggtgacctcc  ttcccggggt  tactgagtcc  cggctcgcgt  gagaagcgct  gcgacccag    1560
ccctgaggtc  acggggccg   gaaggccaga  ggcgccgcgg  ggctggacct  gtcccccaga   1620
gcccgggcga  ctagctgagg  ttcgcgcctc  ttgattgaag  gatcggaatg  gatgcgaag    1680
gggcaggctc  gctgagcgct  cactagcggc  tcctcgcagc  ctctaggatc  gccttagtgc   1740
tgattgcaac  gcgcggtccc  tccagccagg  acccaccggc  ccttgagggt  ccctcttggc   1800
tcccggggtg  gctagtgctt  tgattggcag  agcacagaaa  tccggcggcg  ggggccacg    1860
gaaagactcg  ggcccaggga  ccacggaggg  ggcacctggc  gcggagcccc  caccctaccc   1920
ccggctagct  tgcgtgcgcc  ggcgacatcc  ctctaggggg  cagaggtcag  gcggcccgtc   1980
cccgccccac  ctggcccgga  ggcgcggtgc  ccaggcgttg  cgtgagaagg  accggaggcc   2040
cgcgcagcca  cccagccgac  ccattccccg  gcccggcgcg  ggggctcgca  gtcacgcgag   2100
ggggaaggaa  gtcggggcgg  ggctcttaaa  ggccaccctc  gcgcccggcg  tgggttgggg   2160
tgaggaaaga  actgtgaagg  gtggcgggtg  cgcgattgaa  taaggggatg  cggtgcaaag   2220
ggtctaggtc  tgcgtgtggc  ttctgcctgc  gaggagaggc  agcctgcatg  tgtccgcatt   2280
ttcggtccac  gcctgtggca  cgacacgaag  ccccagtgcc  atttggcatg  gcctagctgc   2340
ctgcctccga  cgctgtcccg  ccctccggaa  ccttcctgtt  acagggtttc  caggaaaaaa   2400
aaagttgtat  ttgcgtgcct  agctcaacct  ggccccagct  aacatcgtta  cgcgccatcc   2460
ccgacgtgct  ccccaacccg  gtggcaccac  catccgtcgc  tggtccaggc  cagaaaataa   2520
tcccctcacc  tcccattccg  gtcatatgcg  gcctcgtgca  ttgcacaaat  atttaccaag   2580
caactactat  gtgccaggag  ctgttcggag  gtgctggcga  ttgacagaga  agggaacaca   2640
gctgacagca  ctcctaatct  cgtggagttt  acattctgat  ggaaggagac  aagtaatatg   2700
ccccaaatct  agagaatgtg  agagggtaaa  aagtgcggtt  gaaaaaaatt  aaacagaaaa   2760
ggcgtacgga  ttatgtgagg  gcagattgca  attcaaaaca  aggggggtcag  ggaaggcctt  2820
gcggagagag  gcaggagtgt  ggagtcaaga  atcaatgtgc  atagatatct  ggataaaaag   2880
tgtacctggg  caggtgcggt  ggctcacgcc  tgtaatccca  ggactttgga  aggccgagtc   2940
gggaggatcg  cctgaggtca  ggagttcaag  accagcctgg  ccaatatggc  aaaaccccat   3000
ctctatcaaa  aatacaaaaa  ttagccgggc  atggtgttgc  tcacctgtaa  tcccagatac   3060
tggggcggtg  agggggtttt  gggggagtg   gagtcaggca  ggagaattgc  ttgaacctgg   3120
gaggcagatg  ttgcagtgag  ctgagatcac  gccactgcac  tccagcctgg  gtgacagagc   3180
gagactccat  ctcaaataaa  agactgcaac  tggcagaggg  aataagcaaa  atcaaagcct   3240
cccgccaccc  cccaccacag  tggttcttga  aggaccgagc  agtaccaggg  atgtgcagag   3300
gtcatgtgac  tgggagttc   tcctggcatg  tagtccaggg  ggatgggatg  cccatgaggc   3360
acagcgccct  gccgcatgtg  cagggagcac  cccattgaga  gacatgagac  ttcctctgtg   3420
cgagatagag  acatggctgg  ggtgtaagag  aagcaaggtc  actcgggcta  ctgtgctaag   3480
aataggagc   acatttctct  gcttggcatc  tgctttggca  tctgtccagc  tccactgcca   3540
caactcatcc  agggcccatc  attgctccct  ggagcactta  gcctccacct  aggttcccat   3600
ttgccttttg  ctccgtccaa  ttacttctcc  atcctgtggc  acccagagtg  gtcctgtcaa   3660
aaatgcaaaa  tctcattcca  tcaccacctt  gcttaaattt  ctttggtagc  tcccaccact   3720
```

```
ctgaaggcag gaataagaat ctttagcagc tctccctctc cctctccctc tccctctccc    3780
tccctctccc tgtcccctct ttccacggtc tccctctgat gccgagccaa agctggactg    3840
tactgctgcc atctcggctc actgcaacct ccctgcctga ttctcctgcc tcagcctgcc    3900
gagtgcctgc gattgcaggc gcgcgccgcc acgcctgact ggttttcgta ttttttttggt    3960 ggagacgggg tttcgctgtg ttggccgggc tggtctccag ctcctaacag ggagtgatcc    4020
gccagcctcg gcctcccgag gtgccgggat tgcagacgga ttctggttca ctcagtgctc    4080
aatggtgccc aggctggagc cgcagtggcg tgatctcggc tcgctacaac ctccacctcc    4140
cacccgcctg ccttggcctc ccaaagtgcc gagattgcag cctctgcccg ccgccaccc    4200 cgtctgggaa gtgaggagcg tctctgcctg ccgcccatc gtctgggacg tgaggagccc    4260
ctctgcctgg ctgcccagtc tggaaagtga ggagcgtctc tgccccaccg ccatcccatc    4320
taggaagtga ggagcgtctc tgcccggcag cccatcgtct gagatgtggg gagcgccttt    4380
gccctgctgc cccgtctggg atgtgaggag cgcctctacc cagccgcgac cccgtctggg    4440
aggtgaggag cgtctctgcc cggccgcccc gtctgagaat caaggagacc ctccgcctgg    4500
caaccgcccc gtctgagaag tgaggagccc ctccgcccgg cagccacccc gtctgggaag    4560
tgaggagcgt ctccgcccgg cagccacccc gtccgggagg gaggtggggg tcagcccccg    4620
ccaggccagc cgccccgtcc gggagggagg tggggggtc agcccccgc cggccagcc    4680 gccctgtccg ggaggaggt gggggggtca gccccccgcc cggccagccg cctcgtccgg    4740
gaggtgaggg gcgcctctgc ccggccgccc ctactgggaa gtgaggagcc cctctgcccg    4800
gccaccaccc catctgggag gtgtacccaa cagctcattg agaacgggcc atgatgacaa    4860
tggcggtttt gtggaataga aagagggggaa aagcggggaa aagattgaga aatcggatgg    4920
ttgccgtgtc tgtgtagaaa gaggtagaca tgggagactc ttcattttgt tctgtactaa    4980
gaaaaattct tctgccttgt gatcctgttg atctgtgacc ttaccccccaa ccctgtgccc    5040 tctgaaacat gtgctgtgtc cactcagggt taaagggatt aagggcagtg caagttgtgc    5100
tttgttaaac agatgcttga aggcagcatg ctcgttaaga gtcatcacca ctccctaatc    5160
tcaagtaccc agggacacaa acactgcgga aggccgcagg gtcctctgcc taggaaaacc    5220
agagaccttt tttcacttgt ttatctgctg accttccctc cactattgtc ctatgaccct    5280
gccaaatacc cctctgcgag aaacacccaa gaatgatcaa taaaaaaaa aaaaaaaata    5340 aggacatgct tgaagcctcc tcaaaccacg agcaataaat ccatcctgca ctcttgaaaa    5400
aaaaaaaaaa agtatcttta gcagaaccta ccaggcctgc ctgcctctag ttctagtgtc    5460
ccctaccttg agtctcagat aaaacatcac ttcctctggg atgccttcct ggattctccc    5520
cccagaaaat tatgtttctc ctggtcgctg tttccagcac ttctccacgg taattcttag    5580
gacactggat acttgctata gccccgaccc aacctgccac ttctttccgt atgctctaac    5640
aaggaaaacc aacctgcagg aaattgatct gataagccaa gtccaggcaa gatattaata    5700
actggtaaag gaattagaca cagctatact atacacaggc caaatggcaa gagagatgtt    5760
gaatccaaag tgctcatgct ataatggtgg aatttaggca acagaacagg caggagacaa    5820
gggaggtatt gctgggcttt ctcagcaccc ttccaattat tctactctct gcatctttga    5880
ttcagtctga ggagcttcat ggtacccaag agaggtctgt ccttcaatcc tagttggagc    5940
tagagccaca gagaacgagc ctgtgtggaa gccatggcaa ggaagtggaa agcaaggcac    6000
tcctagatcc tccaacatgc tctgcagcac aacctcttct tcagcttccc agggtcccca    6060
ccaatgcccc agcgctggag aatcatggca gcctggtcac cagggctgga agaccaacta    6120
```

```
gtgctagggc tcccaaccag ggacccttct cttgatagaa agtgcgttgc tttgcttgca   6180
ttatctaaga ggctcttgac tcctcaaaaa ctcattagct aataaaacca attcgtctct   6240
cacttcttag gtggagagat gggtgccaga aaagaaaagg cccaagtacg catggcaaat   6300
caaagcagag cctagaactc cagcttcttg cttctaggcc agggcccgtc tcaccataac   6360
ttatcatccc agactatgag tgaagcccca gggggccaaa ggtagacaga ctcagcccct   6420
gggccagggc ccctcacctc tccacacccc tggactggtg cactgggggtt acaagagatg   6480 ttgcacttct catcaccaag ccgtatcttg ctaacagtt cacaataaca ggaaggggc   6540 ccacactgag cactgggcag agaaggaggg agtcaggcag gaggttagag gaccttggcc   6600
tggagctgaa cactcattcc tgggtcaaag tttgcatgcc tttgcgtgag aagctctttg   6660
gctaggattc cctagtgatc aataccagga gcagggcag aagtgctggg gaggggaaag   6720
ggctctgggc tggagagatc gagacagctg agaggcctta gcccagcaaa atcatcagcc   6780
tagggctttc agtgagccct gctgaaggct gtgggcaaag gggactggaa gacaagcaag   6840
atccacagca aaccccctgcc ccatggtaga gatgggagtc ataccctaga caagtcctgt   6900
gatgagtctg gagatgctgc aggagctgtg aggaggctgg ggcaggaggg gtgttaaagg   6960
gatgctcccc ggagagtgga gaactagaga aggcccctgg agtctaagga gcataggaag   7020
ggcattccta gcatggggaa gagacacaat gtgaacaaca gatagtagtg ggaggtcggg   7080
gtgaggcagt ttgggtggat gtggagaact gggacttgtc tcccaatgtg tcctctcccc   7140
acccagtcat cccccttctcc tactgagatc tgagcctgag catcttccct tcctctcctg   7200
cctgtgccca gagagccaga tagattgagt ttgcaggata cagggctcag atggggcagc   7260
tcttggctcc ctggctcttg gctgctatag ttaggatgac agtattttcc caggacagtc   7320
taagcctgtt gtcatggaag aattgttaaa agtgccctct ttcactctca aaagatcctg   7380
gcttagatga taataagtta tatagtcacc ccagtgatgg tgggcatggg tgggttttgg   7440
gggcccagca tctgttctcc cttcttttgg caataccaca tcaattgtcc tttcgggatc   7500
acctcacccc tactctcagc ccatagggtt actgtagctg acccacccca ggccaagcca   7560
atgagaaccc tatgggagtt tcccaacacc ccctgccttc tgttgctcgc cagagtgcag   7620
tggtgcgatc ttggctcact gcaaactcca cctcctgggt tcaagcaatt cttctgactc   7680
agcctcccag gtagctggga ttacaggcgc ctgctaccac acccagctaa ttttttttt   7740 ttttttttgt atttttagta gagacggggt ttcaccaagt tggccaggct ggtcttgaac   7800
tcctgacctc aggtgatccc ccctgccttg gcctcctgg gattataggc gtgagccacc   7860
acacctggcc ccctatggga gttttgatga aatcattgga aaagagaggt tctccttctg   7920
tcagaggtgg ctacactggc tagaaagtaa gtctgaagct gccagtagtc atttttaag   7980 gaagccggcc ttagaatgat acctactcaa ggaaaagcag atctgggaga tgaggggagg   8040 aagcggggg gaaattgaag acattaagcc tctagatcca gttattcctg aagtcaatga   8100
agttcaccca tagaaggtcc ctgttaaaaa accaatatca ccatcacctc ccccttctct   8160
tcctgtctcc ctcttttttcc ttcttcttca cccctgcctc attctcttcc tcctcttccc   8220
tctcctcctc ctcctcttct ttcttttcta gtatgaggtg ggtttggggg acttacaact   8280 gcaagaaacac aaacctgcca gccaggaagg cttacctggc agagctctct gagtgactaa   8340
agcctggtac ttgcaggccc caagaagacc tacccaggtt gaacagagtc ctaagaggtt   8400
acttctatct agcagcttcc cactggtctg cttctgtacc taaatggcca ccatccgaac   8460
cactgtggga ggcaaattgt atctccagaa gaccccgtga tggtgtcaag ttgttggctg   8520
```

```
gacagttcct gtgagagaag ccatgtgcgt gacattgttg atcagttgag tctgcgccgt    8580
gtcactgtgc agttcctcct gcactcccag cagtctggga gcagagctca ccaccatgga    8640
ggctggaggc tccttggctc aagcaaata gccaacaagg gaaaggagga gaaaacggaa     8700
cccagagagg gttgctatgg aaaggctata gacaggagct gtggccttca gtagagggtc    8760
acagctagtg ctcaaagacc cgcagagaaa cagcctacat gttccaacct cgctccattc    8820
gtgctctctg tcctgctggt gacttccatg aatggaacct aactggaagc caggatgcaa    8880
agagtccatg aatgcagcct gcataagtta gccctctagg acagtgggca gagaagggtg    8940
gaaagtgagt ctggagagac aagtggaaag catctagtgc tctacccag ggcctttgca     9000 cttgctcctc ccttcaccag caaactttt tttaaagctt gcttgcattt atcttttccc     9060
ccttccccaa ttttatttg tttattttc atacaaatat atggggtaca agtgcaattt     9120
tgttacatgc atagattgca aagtggtcag gccaggactt ttaaggtacc caaaagcatt    9180
gtacaattac ccattaagta atttctcatc atccacctcc tttaccagaa aactcttctt    9240
tcccaaaatc ctcatgtctt acttcctcaa atatcacttt ctcagtatgc cttctcctat    9300
agttttgttt ttgttttttt gagacagtct caccggggttt gcagtggcat gatctcagct   9360
cactgcaacc tctgcctcct gggttcaagc aattctcctg cctcagcctc ccgagtagct    9420
gggattacag gtgcccacca ccatgctcag ctaattttg tatttttagt agagacggga     9480
tttcaccatg ttggccagcc ttgtctcgaa ctcctgacct caggtgatcc accctcctcg    9540
gcctcccaaa gtgctgggat tacaggtgtg agtcaccacg cccagactct catatagttt    9600
ggatgtttgt ctcctccaaa tctcacgttg aaatgtaatc cccaatgttg gaggtggggg    9660
ctggtgggag gtgattgggt catggggtcg gatcctcata aatggtttag caccatcccc    9720
ttggtgctaa gtgagttctc accctaagtt catgtgagat ccgattattt aaaagtatgt    9780
ggcacctccc cctacccttg ttcctgcttt ctcttgcacc cgctttgcct tctgggatga    9840
ttgtaaggtt cctgaggccc gcaccggaag cagatgctgc atccatgctg gtactgcctc    9900
cagaaccatg agccaattac acctcttttc tttatcaatt acccagtctc aggtattcct    9960
taccttcctt ggccatccca cctaaaactg ttaccctgac tcatagtttc tatccttctc   10020
tctacttaat tttatagcac ttagagactc caaacatact gtatatttg cgtatttatg   10080 ttgcagatag gctatatccc tcaactaaaa tgtaagctcc aacagagcag gcactttgat   10140
ctcttgtgat caatgcttca cgaatagcat ctagcacata gcagatgcta aatagatagt   10200
tgttaaataa ttgaatttaa gcgtggcagg cccccaagtg ggaaaataca cgagatttga   10260
agtggcagag gccttgtgtg agagtctggt tcctggtagg cagggcacca agtccaagac   10320
agtcagctga atggatcccc tcagctcaga tgcttttta atgcctgcta gatgggcgtt    10380
aatcattttg ctcccaggag ataggtgatc aggtacactc ctgccttaag aagttcatct   10440
tggtctggcc tagcttagca tcctgccttg tgccagcttc actctatcca agaccaacat   10500
ctgggctggg tctcactgcc aaccacatgg ccatgatcct cagactttcc caacctcctc   10560
caattttaaa gtctccaggt tcctcccaac aggatggctt ctctctacac accccagata   10620
caccacagta atcaggggag atcaggctct gcagctgctc tcagcaggat tgggacaaaa   10680
atcctccatg ttttggtggg tggggaaggg ctatgaagat ccagcctccg ggatgctgcc   10740
cagagaaagc tggggagcag gtggcccaga gcttctggac tgaccctaga tggagggcag   10800
tggagatgaa aggagatctt cttttcctt tctcttctgc ctttaataac atcaaatatg    10860
attaatttag gtccatatta tagatgagaa tttgactaat tcttctcagg ttagcagttt   10920
```

```
attattgcac aaatgtttcc caagccaatg aattatgaaa taagccttgc aggggaatgt    10980
ttgagctact gaagggcatg ttcggcatga tcagaggaac actctgtttc caagttagta    11040
atgtctcttt acatataaac actgatgttt gttgataatg aacattcatg tcctcaatca    11100
aagcagagcc tctggggaca cttctctatc agccaagtgc tcctagaagt gttccgccct    11160
ggttagaatg tgcgcccaa ttttcatgtg ttggaaacat aatcccaaaa ttcatatgtt    11220
gattaaaggt agtgagggct ttgggaagta attaagatta gataaggtca tcaaggtggt    11280
actcccatga tgagactgga ggcttataa gaagaggaag agagacctga gctgacacca    11340
cactcttgcc ctcttaccat gtaatgcccc ctctgtgttt tggtgttttg gcttgttttg    11400
tttgtttgtt tgtttgtttt tgagattgag cctcactctg tcactcaggc tggagtgcaa    11460
tggtgtgatc tcggctcact acaaccacca cctcccaggt tcaagtgatt ctcttgcctc    11520
agcctcccaa atagctggga ttacaggcat gcaccaccac acccggctaa ttttttgcatt    11580
tattcagtag acgggatt ttcaccatat tggccaggct ggtctggaac tcctgatctc    11640
aagtaatcca cctacctcaa cctcccaaag tgctgggatt acaggtgtga gccaccacgc    11700
ctgacctagt cagtggtatc ctgttatagc aaccgagaac agactgagac atacatgctc    11760
ccatggtctt tgccaaggag gtagcctatt cagatccact ggggtgtcca gccagtgagg    11820
gccactcagc caacttacga atccttttcc aactcaactg ctccatcact tgtagacacc    11880
caatagccct tcctcccaat cttgatttt cctccttagc actcaccgct cttgttttgt    11940
ctaggaaccc tccatcttcc tttctagaac tatgtgcttt aggggaagct gacccccagcc    12000
ccagcctcac agagtgggtc ttggctgatc tgaaccagtc attgttgccc tggctgtctt    12060
gctggtgatt taattaaaca tagatctgtg acatgattct ggccaatgat atgggaaaaa    12120
atctgctggg acaacttta ggagaagctt tcttcactct tcaaagagac acatgagaat    12180
gaaactagac ccctgtctct caccatatac ataaatcaaa accaaaatgg attaaaggct    12240
tcaatctaag accacaaact atgaaattac taaaaggaag cattgggaaa actctccagg    12300
actggacaaa aattcctctt ttctttttt ctttctttt ttttttttt tttttttt    12360
gtagaggcac agtctcaact atgctaccca ggctggtctc aaacttctgg gctcaagcta    12420
tcctcctgcc taggtctcac aaagtgctgg aaatcatagg catgagccac cttgcctggc    12480
ccggacaaag atgtcttgag tgatatctta caagtacagg ctgaagcaaa aatgacaaa    12540
tgagatctca tcaagttaaa aggcttctgc acagcaaagg aaacaatcaa caaagtgaag    12600
agacaatcca cagaatggga gaaaatattt gcaaactacc catctgacat gggattaata    12660
actggaatat ataaggagct caaacaactc aacaggaaaa agtctaataa tctggctttt    12720
aaatttaatc tggcaaaaga tctgaataga catttctcaa aagaagaaat acaaatggca    12780
agcaagtata tgaaaaggtg cttaacatca ttgatcagag aaatgcaaat caaaactaca    12840
atgagatatc ctctcaccag ttaagatggc ttttgtccaa aagacaggca atgacaaatg    12900
ctggagagga tgtggaggaa agggacctt cgtacactgt tgaaaatgta aatcagtgta    12960
aacactacaa agaacagttt ggaggttcct caataaacta aaaatagagc taccatcga    13020
tccagcaatc ccactgttac gtatacaccc aaagaaagga aatcagtatg tcaaagagat    13080
atttgcactc ccatgttgac tgcggcattg ttcacaaaag ttaagatttg gaagcaacct    13140
aagtgtccac caacagatga ataggtaaag aaaatatagt gcatatacac aatggagtgc    13200
tattcagctg taaaaagaat gagatccggc cgggcgcagt ggctcacgcc agtaatccca    13260
gcactttgga aggcgtagga gggcggatca tgaggtcagg agatagagac catcctggct    13320
```

```
aacacggtga aaccccgtct ctactaaaaa tacagaatat tagccgggca tggtggcggg    13380
cacctgtagt cccagctact caggaggctg aggcagaaga tggcgtgaa cccgggaggc    13440 ggagcttgca gtgagccgag accacaccac tgcactccag cctgggcgac agagcgagac    13500
tccgtctcaa aaaaaaaaaa aaaaaaccaa tgagatcctg tcatttgcag caacacggat    13560
ggaactggag gtcattatgt tgagtcaaat aagccaggca cggggagaca aacttcacat    13620
gttctcactt atttgagagc tgaaaattaa aacagttgaa ctcatggaga taggagaatg    13680
atggttacta gaggctggga agggtagtgg gagcagggag ggagtaggga tgattaatgg    13740
gtacaaaata tagttagaaa gaatgaataa gatctagtat ttgatggcac aacaagatgg    13800
ctacagtcaa tgtattagtc cgttttcact gttgataaag acatagccga gactgggcaa    13860
tttacaaaag aaagaggttt aatggactta cagttccgcg tgggtgggga ggcctcacaa    13920
tcatggcaga agatgaaagg cacatctcac atggtggcag acaagagaag acagcttgtg    13980
cagggaaatt cccctttta aaaccaccag atctcatgag acttattcac tatcacgaga    14040
acagcacagg aaacacctgc ccccatgatt caattacctc ccactgggtc cctcccacag    14100
catgtgggaa ttcaagatga gatttaagtg gggacacagc caaaccatat tagtcaatga    14160
aaatttattg tacattatta ataactgaa agaatagatg tctgtaacac aaaggaagga    14220
taaatgtttg agatgatgga tacctcattt aacccgatgt ggttattaca cattgtatgc    14280
ctgtatcaaa atatttaatg tgccccataa acatatacac ctactatgta cccacaaaaa    14340
ttaaaaatta aaattaggct ggacacggtg gctcacgcct gtaatcccag cactttggga    14400
ggcccaggtg gggttatcac ttgaggtcag gaggtcaaga ccagcctggc caacatagtg    14460
aaaccttgtc tctactaaaa agacaaaagt taaccaggag tggtggcatg cacctgtaat    14520
cccagctact tgggaagctg agacatgaga gtcacttgaa cccaggaggc agaggttaca    14580
gtgagccaag atcgtactac tgcactccag cctgggtgac agtgagactt catcttcaaa    14640
aaataataat aataataggc tgggtgctat tgctcacgcc tgtaatccca gcactttggg    14700
aggctgaggc gggcagatca cgaggtcagg agatcaagac catcctggct aacacagtga    14760
aaccctgtct ctactaaaaa tacaaaaaaa ttagccgggc atggtggcag gcatctgtag    14820
tcccagctac ttgggaggct gaggcaggag aatggcatga acccaggagg cagagcttgc    14880
agtgagccga gatcgcgcca ctgcactcca gcctgggcga cagagtgaga ctccatctca    14940
aaaataataa taataataat aataaaataa attaaattaa ataattgcaa ggtgtgggga    15000 gttttctga aagggggata agtggcaaga gatacactct agtctctctg gcctttgtca    15060
ggtgtggatg atgtgatggc cagagctacc gcagccatct tgtgaccaca agggagccag    15120 cgtggggga agctgcattc aaagattagc agtgcaaaaa tgcagaaaga tcctgcattt    15180
ttcaggatcc tggtaataaa cagaggatcc actcaaactg gattattaga agaattcaat    15240 aaggggcta tttacaaaag tgcaggcaga gcatagagaa actaacccag gatagtgtag    15300
taccaatgga ctagtaacgg aggggagccc tcaccacctt gggcctgaag gagcaagggg    15360
caggaaccca gagagacact ataaggagag gagagctgcc tagcaggtgt cttcacagac    15420
agggtctgga ggggaacaac cccaaactca ttcttctcct acccgcccat cttatgccag    15480
tgccttccat tggctgaacc caacaagaag ccagtgggcg gggagcccat ggacaatatg    15540
cagaggtcat cctcccagaa cacagagact cgcagagtga tctagaggac aaaggatttt    15600
cagcactacc cggcctgca attatctttt tcatctgttt gcctgcatat tggcggtctc    15660
ctccctgaag gcaggaactg ccttactgct gtaagttttcc tcctagaaca gcggatggct    15720
```

```
gcacaactta cgctcaaaga atatggttga gcacccacta tgcagcaggc actgtactag    15780
aaatcaaatg aagccgggtg tggtggctca cgactatgat cccagcaatt tgggaggctt    15840
aggcaggagg attgcttgag cccaggagtt taagactagc ctgggcaaca tgatgagacc    15900
ctggatctac aagaattttt taaaattagc caggcatggt ggtgtgtgcc tgtggtccca    15960
gctatgcaag agactgaagg ggaggattgc ttgagcccgg gaggtcgagg ctgcagtgag    16020
ccatgatggt gccactatac gccagcctgg gcaacagagc aagactctcc aaaaaaaaaa    16080
aatcaaatga ataaaacata gcgtgcctca gttgttcaca agctggagag ggagagtaaa    16140
accaaagcaa tatggcatct tggtgtcata ccaggagaga gacatgccca aggaaggagg    16200
ctctgaccag agtagggcct ggaggaggtg ggcctggtac caagtgttga aggacttgtt    16260
ttaatggaga ggtgaggatg ctttgtcatt aatgcatcat aatattgcag tatgagtaag    16320
tatctctaac ccaaaagcaa tgcatttcct tgagggtgtt tgttgaatgg ggaagaagtg    16380
gttggaagga aggttgggtg ttccaaacag agggaacatc atgtgtgcat gcagaaagac    16440
agaaaactag agaaattgtc cccactggct ggtgggaaaa ttgtgtgagg aggaagggat    16500
gggaaatgag gtgagagaag agtaggaact ggctcacatg ttgagctgag gagttcaagc    16560
tttgttctga atgcctgaag aaattgataa gggattttga ttagagatct gacatgctca    16620
gatttgcaac ttcagagact tcacttgagt ggcagcgtgg agtgtgtgga ttggaaggat    16680
gagggagcag gaagccttag agctttgtgt ggctacttaa atttaaaatt aggccaggcg    16740
cagtggctca cacctgtaat cccaacactt tggaagacca agatgggctt gttgcttgag    16800
cccaagagtt cgagaccagc ctgggcaaca tggtgaaact ccatctctac aaaaaaatac    16860
aaaaaattag ctggatgtgg tggcatgcat ctgtattccc agctatttgg gaggctgaga    16920
tgggagaatc acctgagccc atgaggtcaa ggttgcagtg agccaaggct gtgccactgt    16980
actccagcct gagcaacaga gtgagaccct tttttaaaaa caaaacgaaa aaactagtat    17040
tcacctcaca gggtggctat aaagctaaaa cagggatggt tcgtgttaac catgtagcac    17100
agagcttggg gcatagtagg tgctcaataa atcttaatgc attattcctt gcaatttcca    17160
taaaaccaat gcaggaaatg cccccaagca gagtcttcct aaagttcttg gcaggtgagc    17220
attcttactt gtgaacacta attgattcaa taaatgtttt tctgaatagg tgttcctcag    17280
taactgtggg gaattggttc caggacctcc ccactagcca tggataccaa aatctatgga    17340
tgccaaagtc cctgatatac aatggcataa aatttgcata taatctttgc atagtatttg    17400
catataatct atactttaaa tcatctccag attacttgta gtatctaata caacataagt    17460
gctatataca gagttgttgg ccgggcgcag tggctcatgc ctgtaatccc agcactttgg    17520
gacaccaagg caggaagatc acctgaggtc gggagtttaa gaccagcctg agcaacatgg    17580
agaaacccca tctttactaa aaatacaaaa ttagccgggc atggtggcgc atgcctgtaa    17640
tcccagctac tagggagact gaggtaggag aattgcttga acccgggagg cggaggttgc    17700
agtgagccaa gactgtgcca ttgcactcca gccttggaaa caagagcaag actccatctc    17760
aaaaaaaaaa aaaaaaaaga tttgttagtt atactatatt attagggaa taatggcaag    17820 aaaagtaagt ttgtacatgt tcagtaccga tgcaaccatc catcttttt ccgaatattt    17880 tccatctgtg gttggttgaa tccatggaac ctacagatac gagggccaac tgtgtggctg    17940
catgccagcc cctgcgttgg agactagaga taggaagaaa ggcagaagct gccttgacct    18000
tcaaggagct caaagtccag aggggcaacg tgttacggaa tgctgctaag gagggcagta    18060
tggaggctgt gggaacttaa ctgcggggga gctgagactc agacagtgtg gtgacagctg    18120
```

```
agcagggtat aaaatgatga gccaaagtgg ccggggaatg cagggtgggg agaaggtttc   18180
aagcaaaggg atcagctttg gagaaagaca gtaaaggtgg gggcaagggt gacatggggg   18240
gcaacagagc cagagagtga acagaaactg ctgctgaagc ctttgggtgt aagcaaaaga   18300
gttggtttta tcctgaaatc tctggggaat attgaagcac ttttaaaagg gaagtagtca   18360
acatacctcc agagtggctc aaatgaaaaa gatcaaaaat atccagtggt ggccaggcgt   18420
ggtggctcat gcctataatc ccagcacttt gggaggctga agtaggtgga tcatctgagg   18480
tcaggagttc aagaccagcc tggccaacat ggtgaaactc tgtccctcct aaagatacaa   18540
aaattagctg gcatggtgg tgggtgcctg taatcccagc tactcggaag gctgaggcag   18600
gagaatcatt tgaacttggg aggcggaggc tgcagtgagc agagattgtg ccactgcact   18660
ccagcctggg tgacagagcg agactccatc agaaagaaag agagagagag agagagaaag   18720 aagaaagaa agaaagaaag aaagaaagaa agaagaaaag aaagaaagaa agaaagaagg   18780
aaagaaagaa agaagagggg aggagggag gaagggaggg aaggagggaa ggaaggaagg   18840
aaggaaggaa ggaaggaagg aaggaaggaa ggaaggaagg aaggaagaaa gaaagaaaat   18900
atccagtggt ggtgaggatg agaagcagct ggagcctcat acacaccggg tgggggtata   18960
aactggttca actgcttagg aaagttggag tttttgtttg tttgtttgtt tgtttgtttg   19020
tttgtgagac agggtctcac tctgtcaccc aggttggagt gcagtggcac tatctcggct   19080
cactgcaacc tcctccgcct cccgaattca acgattctt gtgtgtcaac ctctcgagta   19140
gctgggacta caggtgcaca ccaccacacc cagctaattt ttgtattttt agtagagaca   19200
acgttttgcc atgtttgcct ggctggtctc aaactcctga gctcaagcga tctgcctgcc   19260
ttggcctccc aaagtgctgg gattacaggt gtgaaccatt gcacccagcc aggaaagttg   19320
tttggtagaa tatattactg ctggacattc acctatccta tgaactagca attccagcct   19380
gagcagcaaa catgcattca aaagcaggtt cgagaatgct cctggatggg cacggtggct   19440
cacgccggta atcccagcac tttgggaggc caaggaggac agatcacctg agttgggagt   19500
ttgagaccag cctgaccaac atggagaaac cccatctcta ctaaaaatac aaaattagct   19560
gggcatggta gcctgtaatc tcagctactc aggaggctta ggcaagagaa tcgcttgaac   19620
cgggaaggca gatgtggtga gccgagatca cgccatcgca ctccagcctg gcaacaaga   19680 gctaaactct gtctcaaaag aaaaaaaaaa gatgctcctg acagcagggc tcatcttagc   19740
ccaacagagg aagcaaccga agtatcaatc aacagttgaa tgaatgaata aggtgttggg   19800
tattcatatt ataatggaat accgtgcagc aatgagaatg aactataact atgcccaaca   19860
tcatgaatga gtctcataaa aaagaatgt taagtaacag aaaccagaaa ccagacacaa   19920
gattatatac cgcccactga aatgtatact taaaatggtt aaaatggtaa attaaaattt   19980 ttttttaaaat agagatgggg tctcactatg ttgcccaggc tggtcttgaa ctcctgggct   20040
taagcgatcc tcccacctca gcctcccaag tgctagggtt acaggtgtga gccaccatgc   20100
ctggccctat agtgttaaat gttatgttat gtatattatt tcaccacaac caaaaaagtg   20160
taggtggggg accatagaac tgtacaacac aaagtgcatc ttaatttaaa ctatggtcgt   20220
cggttaataa taatgtatca cgaggctggg cgtggtggct cacacctgta atctcaacac   20280
tttgggaggc cgaggtgggc agatcacctg aggtcaggag tttgagacca acctggccaa   20340
cacagtgaaa ccccgtctat actaaaaata caaaaattag ccgagcatgg tggtgtgtgc   20400
ctgtaatcct agctactcag gaggctgagg caccagaatc gcttgaatct gggaggaaga   20460
ggttgcagtg agctgagatt gtaccaccgc acttcagcct gggcaacaga acaaaacttt   20520
```

```
gtctctcttt attttatttt attattttt ttgagacgag tcttgctcta tggcgcaggc   20580
tggagtgcag tggcgcgatc ttggctcact gcaacctcca cctctggggt tcaaaggatt   20640
ctcctgcctc agcctccctg agtagctggg actacaggca tgcgccacca tggtcggcta   20700
attttttgt attttagta gagatggggt tttatcatgt tggccaggct ggtccagaac   20760
tcctgacctc aagtgatccg cccacatcag cctcccaaag tgctgagatt acagatgtga   20820
gcctccacac caggcctgag actctgtctc aaaacaacaa caacaacaac cagaatgtat   20880
caatattcat ccacgaattg taacaaatat attacaccac tgcaagatgt taataatagg   20940
ggaaactgca gagtgggggt ggtaaatggc cactttacc tccctcatca tactttccac   21000
tcaatttttc tgtgaaccaa agactgctct aaaaaaatct attagctttt traaattcct   21060
tggctcccct ccaaaaagtg tacatatgac atgatctcat ttatgtaaaa tacaacaagc   21120
aaaacaaatc catgcaatag atgttgggt catgggtacc cttgagaaag gaacacaacg   21180
ggacttcttg gatgcttatg atgtctcttg attagagctg gttatatgtg tgtttgttaa   21240
gtttgcaaaa attcatcaag ctacacatga tcgagctata catgacatat gcacttttcc   21300
atttatttat ttatttttga cagaatct tgctctgtca cccaggctgg agtgcagtgg   21360
tgcgatcttg gctcaccgca acctccgcct ctcggattca agcaattgtc atgccccagc   21420
ttcccgagta gctggaatta caggtgtgca ccatcacgcc cagctaattt ttttttgtat   21480
ttttagtaga gatgaggttt cactatgttg gccaggctgg tcttgaactc ctggcctcac   21540
tcaagtgatc ctcccacctc ggcctcccaa agtgctagaa ttacaggtgt gagtcaccgg   21600
tcccagctga catatgcact tttctatatt gtatcctgta atttaatttt tttaagtttt   21660
aagaaaacat taaaatawa aagataaata gtctgtcata caggagaatt tcaaatagtt   21720
tatggagata atcccccctc aaggagaagg agcgtaatcc cccactcctt cggtgtgggc   21780
tgtgcatagt gacttccttc caaaaggtac agtatggaaa ggtgggaaag gagtaacttt   21840
acagtgaaga gacctgacac gcactacctt agccaggtga tcaaggtcaa catccacatc   21900
tgtaagtcac attgatagga gtaaccctg atatgatgtg acgagaatgg caccntaacc   21960
tccaaggtct tcccaccaac aaaccataac cccaggcgtt ccatgagaag aaaaacatca   22020
ggcacattcc aakrgtscga gcatcctaca aaatgtccaa ccagtactcc tgaaaattgt   22080
caaggtcatc aaaaacaagg atatcctgag aaactgtcac agccaagagg aatccaaaga   22140
gacgtgatga ctaaatgtca tgtgatatcc aatgggtcct ggaacaggaa aaggacatta   22200
ggtaaaacgc aaggaaatct aagtaaacca tgaactttag ttaattagag agacagacag   22260
acagagagaa agaaagagtc cattttctat aaaaccgagc ctaacctcaa accttgacct   22320
tttcattga gtcatctgaa cccaatggag atatagacag gaaacaactt tcctcttctc   22380
ccattcatgg ccttcaaaca tgctctgttt ctctattgga ttccccatcc atctgccttg   22440
gcatcttcac aggttgatcc cacagtttc tcattttcag gaataaaagc ccactccagt   22500
ctaaatcaaa acttccctct cacatccatg ccgggcacag tggctcacac ctgtaatccc   22560
agcagtttgg gaggccaagg cagaaggatt gcttgggccc agaagttcaa gaccaacctg   22620
ggcaacatgg caagacctcc tctctacaaa aaaatgttta aaaataaaaa aattagccag   22680
gcatggtgca cacacctgtg attgtggtcc cagctactca ggaggctgag gcaagaggat   22740
tgtttgagct caggaggtcg aggctgcagt gagccatgat tgtggacat gaaccccaac   22800
ctgggtgaca gagcaagact ctgtatctaa aaaaaaaaaa aaaagatagc aaacttcctt   22860
ttcacatcca atttaaggct tgtcctcctc ctcctcttag atctgactga gatctgggtc   22920
```

-continued

| | |
|---|---|
| catattaaag actcctttag tacaacaaac accatatatc ctcacgtaag tccatgaata | 22980 |
| tctgacattt ctcatatcta ctttctctcg atttattgat agataggtat acattgtttt | 23040 |
| aattttatgg gtacatagta ggtgtatata tgtatggggt acatgaaatg ttttgataca | 23100 |
| ggcatgcaat atgaaataag cattcatgga gaatggagta tccatcccct caagcaagga | 23160 |
| taaacctttg agttacaaac aatccaatta cactctttaa aggtgtacat ttttttttt | 23220 |
| tttgagacgg agtctcactc tgtcgcccag gctggagtgg agtggcacga tcttggctca | 23280 |
| ctgcagcctc cacctcccaa gttcaagcca ttctcctgcc tcagcctccc gagtagctgg | 23340 |
| gatcacaggc acatgccacc atgcctggct aattttttgta tttttagtag agacggagtt | 23400 |
| tcaccaggtt ggccaggctg gtcttgaaca cctgatctca ggtgatccgc ccatctcggc | 23460 |
| ctctcaaagt gctgggatta caggtgcgag ccatcgcgcc tggcctagag gtgtacattt | 23520 |
| tttaacagaa ccattcaaaa ggaggttgtg gggatcatga cacttccatg ctacagcatt | 23580 |
| aatctcctaa gaataaggat acactcccac ataccatgac actctgttca cacctaaaaa | 23640 |
| aatttacatt tattccagaa tatcatctaa tctccagtcc gtgcttacat gtccccaatt | 23700 |
| gtccccaaaa catcttttat agattttttt aaaattttgt ttaaatgcca tatccaatcg | 23760 |
| atatggcaat caaatgcaaa tccatattgc atttggttat gtctcttagt cttttttgcat | 23820 |
| aaggggggcc tctctttagg atgcaaaatc tttatcatct cttcttttcc acttggggac | 23880 |
| ttgggctgaa aatcaggagt ggctggaaca cgcccattta ctgtttggtt ttgcaggttg | 23940 |
| ttggagggta ctacagaaga acatccctct ggagagggggc cgtgagcctg gttggcctag | 24000 |
| actgagtgcc ctggcagagc tcttcctcat gtgtgcagtg ggaaagaagc ccagatcagt | 24060 |
| ccaaaggcct aaccccccact cccagaccct accctactct tcagagaaat aggctcccta | 24120 |
| ccctgaaccc taaagacagc tgtaccttca tccccaggga cccagcaccc cttctggcct | 24180 |
| atccccaaag agtcaccctg ggtcttaggt agtaggtgga gctgagggat aatggcccaa | 24240 |
| ggccaagagt tgatccttcc aactttgttc agtgatccag ctttcatatc aggtgatcag | 24300 |
| gacaaccagg ccaatctgat aggggcggt gtttataaaa aggccactca cctagagcca | 24360 |
| gaagctccac accagccatt acaaccctgc caatctcaag cacctgcctc tacaggtacc | 24420 |
| tttcttggga ccaatttaca atctctgg | 24448 |

<210> SEQ ID NO 2
<211> LENGTH: 51
<212> TYPE: DNA
<213> ORGANISM: Artificial sequence
<220> FEATURE:
<223> OTHER INFORMATION: Description of Artificial Sequence: Synthetic
    primer

<400> SEQUENCE: 2
gcggtcgacg gccggccgga tctcattctt tttacagctg aatagcactc c                51

<210> SEQ ID NO 3
<211> LENGTH: 39
<212> TYPE: DNA
<213> ORGANISM: Artificial sequence
<220> FEATURE:
<223> OTHER INFORMATION: Description of Artificial Sequence: Synthetic
    primer

<400> SEQUENCE: 3
gcggaattca tcttggaggt ggctgctgag agaaggtgc                              39

<210> SEQ ID NO 4

```
<211> LENGTH: 36
<212> TYPE: DNA
<213> ORGANISM: Artificial sequence
<220> FEATURE:
<223> OTHER INFORMATION: Description of Artificial Sequence: Synthetic
      primer

<400> SEQUENCE: 4
gcgctcgaga gaataccagg cagaagatgg cagagg                              36

<210> SEQ ID NO 5
<211> LENGTH: 55
<212> TYPE: DNA
<213> ORGANISM: Artificial sequence
<220> FEATURE:
<223> OTHER INFORMATION: Description of Artificial Sequence: Synthetic
      primer

<400> SEQUENCE: 5
gcgacgcgtg gccggccata tagtgcatat acacaatgga gtgctattca gctgt        55

<210> SEQ ID NO 6
<211> LENGTH: 32
<212> TYPE: DNA
<213> ORGANISM: Artificial sequence
<220> FEATURE:
<223> OTHER INFORMATION: Description of Artificial Sequence: Synthetic
      primer

<400> SEQUENCE: 6
tcccagctac tcgagaggtt gacacacaag aa                                  32

<210> SEQ ID NO 7
<211> LENGTH: 46
<212> TYPE: DNA
<213> ORGANISM: Artificial sequence
<220> FEATURE:
<223> OTHER INFORMATION: Description of Artificial Sequence: Synthetic
      primer

<400> SEQUENCE: 7
cgacgcgtcc cgctcgagga tcctcataaa tggtttagca ccatcc                   46

<210> SEQ ID NO 8
<211> LENGTH: 24
<212> TYPE: DNA
<213> ORGANISM: Artificial sequence
<220> FEATURE:
<223> OTHER INFORMATION: Description of Artificial Sequence: Synthetic
      primer

<400> SEQUENCE: 8
ctgagtcccg gcagaagcgc tgcg                                           24

<210> SEQ ID NO 9
<211> LENGTH: 24
<212> TYPE: DNA
<213> ORGANISM: Artificial sequence
<220> FEATURE:
<223> OTHER INFORMATION: Description of Artificial Sequence: Synthetic
      primer

<400> SEQUENCE: 9
cgcagcgctt ctgccgggac tcag                                           24

<210> SEQ ID NO 10
<211> LENGTH: 20
<212> TYPE: DNA
```

```
<213> ORGANISM: Artificial sequence
<220> FEATURE:
<223> OTHER INFORMATION: Description of Artificial Sequence: Synthetic
      primer

<400> SEQUENCE: 10
gcgtgctagc cgccggcgac                                               20

<210> SEQ ID NO 11
<211> LENGTH: 20
<212> TYPE: DNA
<213> ORGANISM: Artificial sequence
<220> FEATURE:
<223> OTHER INFORMATION: Description of Artificial Sequence: Synthetic
      primer

<400> SEQUENCE: 11
gtcgccggcg gctagcacgc                                               20

<210> SEQ ID NO 12
<211> LENGTH: 24
<212> TYPE: DNA
<213> ORGANISM: Artificial sequence
<220> FEATURE:
<223> OTHER INFORMATION: Description of Artificial Sequence: Synthetic
      primer

<400> SEQUENCE: 12
gtgcccaggc gagaaggacc ggag                                          24

<210> SEQ ID NO 13
<211> LENGTH: 24
<212> TYPE: DNA
<213> ORGANISM: Artificial sequence
<220> FEATURE:
<223> OTHER INFORMATION: Description of Artificial Sequence: Synthetic
      primer

<400> SEQUENCE: 13
ctccggtcct tctcgcctgg gcac                                          24

<210> SEQ ID NO 14
<211> LENGTH: 28
<212> TYPE: DNA
<213> ORGANISM: Artificial sequence
<220> FEATURE:
<223> OTHER INFORMATION: Description of Artificial Sequence: Synthetic
      primer

<400> SEQUENCE: 14
cgggggctcg cagtgggggg agggagtc                                      28

<210> SEQ ID NO 15
<211> LENGTH: 28
<212> TYPE: DNA
<213> ORGANISM: Artificial sequence
<220> FEATURE:
<223> OTHER INFORMATION: Description of Artificial Sequence: Synthetic
      primer

<400> SEQUENCE: 15
gactccctcc ccccactgcg agccccg                                       28

<210> SEQ ID NO 16
<211> LENGTH: 38
<212> TYPE: DNA
<213> ORGANISM: Artificial sequence
<220> FEATURE:
```

```
<223> OTHER INFORMATION: Description of Artificial Sequence: Synthetic
      primer

<400> SEQUENCE: 16
ccaggaaaaa aaaagttgta tcctagctca acctggcc                              38

<210> SEQ ID NO 17
<211> LENGTH: 38
<212> TYPE: DNA
<213> ORGANISM: Artificial sequence
<220> FEATURE:
<223> OTHER INFORMATION: Description of Artificial Sequence: Synthetic
      primer

<400> SEQUENCE: 17
ggccaggttg agctaggata caacttttt tttcctgg                               38
```